US011273445B2

(12) United States Patent
Kim et al.

(10) Patent No.: US 11,273,445 B2
(45) Date of Patent: Mar. 15, 2022

(54) BIOMIMETIC CHIP DEVICE

(71) Applicant: Daegu Gyeongbuk Institute of Science and Technology, Daegu (KR)

(72) Inventors: Jin Young Kim, Daegu (KR); Hong Soo Choi, Daegu (KR); Eun Hee Kim, Goyang-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 148 days.

(21) Appl. No.: 16/674,347

(22) Filed: Nov. 5, 2019

(65) Prior Publication Data

US 2020/0139364 A1 May 7, 2020

(30) Foreign Application Priority Data

Nov. 5, 2018 (KR) .................. 10-2018-0134448
Oct. 18, 2019 (KR) .................. 10-2019-0130188
Oct. 18, 2019 (KR) .................. 10-2019-0130189

(51) Int. Cl.
*B01L 3/00* (2006.01)

(52) U.S. Cl.
CPC ..... *B01L 3/50273* (2013.01); *B01L 3/502738* (2013.01); *B01L 2300/047* (2013.01);
(Continued)

(58) Field of Classification Search
CPC ........... B01L 3/50273; B01L 3/502738; B01L 2300/047; B01L 2300/087; B01L 2400/06; B01L 2400/0457; B01L 2300/0819; C12M 23/42; C12M 21/08; C12M 23/16; C12M 27/16
See application file for complete search history.

(56) References Cited

U.S. PATENT DOCUMENTS

2009/0203126 A1* 8/2009 Hung ................. B01L 3/502715
435/325
2013/0130232 A1* 5/2013 Weibel ................ B01L 3/50273
435/5

(Continued)

FOREIGN PATENT DOCUMENTS

KR   10-1784233    10/2017
KR   101803325     12/2017
WO   WO 2007/085395 A1   8/2007

OTHER PUBLICATIONS

Office Action issued on Korean patent application 10-2018-0134448 dated Mar. 6, 2020, 5 pages.
(Continued)

*Primary Examiner* — Jennifer Wecker
*Assistant Examiner* — Oyeleye Alexander Alabi
(74) *Attorney, Agent, or Firm* — Lex IP Meister, PLLC

(57) ABSTRACT

Provided is a biomimetic chip device. The biomimetic chip device includes a body, a main channel arranged in the body and extending in one direction, a plurality of culture chambers spaced apart from each other on the main channel, a first reservoir arranged at one end of the main channel and storing a first fluid, and a second reservoir arranged at the other end of the main channel and storing the first fluid, wherein the body is tilted about a first axis perpendicular to the one direction to allow the first fluid to flow between the first reservoir and the second reservoir.

10 Claims, 18 Drawing Sheets

(52) U.S. Cl.
 CPC . *B01L 2300/087* (2013.01); *B01L 2300/0819* (2013.01); *B01L 2400/0457* (2013.01); *B01L 2400/06* (2013.01)

(56) References Cited

U.S. PATENT DOCUMENTS

2015/0301027 A1* 10/2015 Charest .................. C12M 23/16
 435/29
2016/0137967 A1* 5/2016 Tajima ................... C12M 33/00
 435/173.9
2016/0312165 A1* 10/2016 Lowe, Jr. ............... C12M 23/16

OTHER PUBLICATIONS

Jin-Young Kim et al., "96-Well Format-Based Microfluidic Platform for Parallel Interconnection of Multiple Multicellular Spheroids", J Lab Autom. Jun. 2015;20(3):274-82. doi: 10.1177/2211068214564056. Epub Dec. 18, 2014.

A.A. Gladkov et al., "Study of Stimulus-Induced Plasticity in Neural Networks Cultured in Microfluidic Chips", CTM, 2017, vol. 9, issue 4, pp. 15-24, DOI: http://doi.org/10.17691/stm2017.9.4.02.

Ilka Maschmeyer et al., "A four-organ-chip for interconnected long-term co-culture of human intestine, liver, skin and kidney equivalents", Lab Chip, 2015, 15, 2688, May 13, 2015.

* cited by examiner

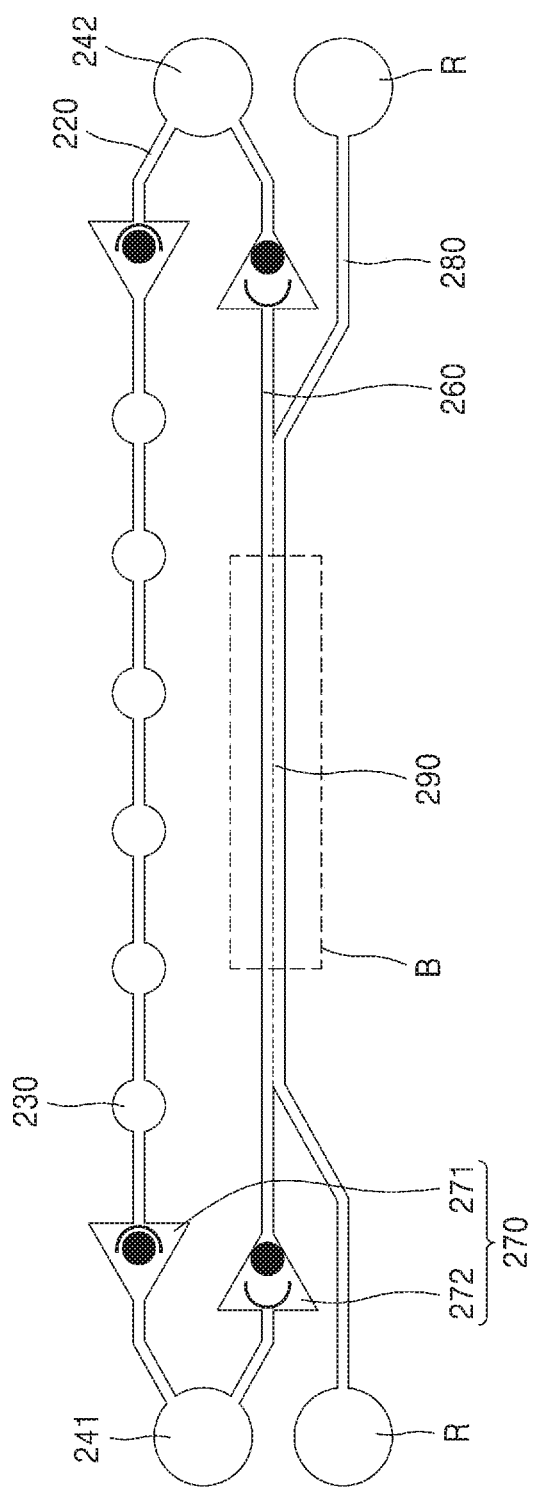

BIOMIMETIC CHIP DEVICE

CROSS-REFERENCE TO RELATED APPLICATIONS

This application claims priority to Korean Patent Application No. 10-2019-0130188, filed on Oct. 18, 2019 in the Korean Intellectual Property Office, Korean Patent Application No. 10-2019-0130189, filed on Oct. 18, 2019 in the Korean Intellectual Property Office, and Korean Patent Application No. 10-2018-0134448, filed on Nov. 5, 2018 in the Korean Intellectual Property Office, the disclosures of all of which are incorporated herein in their entirety by reference.

BACKGROUND

1. Field

The present disclosure relates to a biomimetic chip device.

2. Description of Related Art

When developing food or new drugs, a preclinical test is a step for assessing the efficacy and toxicity of ingredients. In this preclinical test, human or animal cells may be used to predict side effects and efficacy. However, since the accuracy of cell culture models is not high, high development costs and much time are required.

Accordingly, on-chip cell culture technology is being applied to preclinical tests performed during food or drug development. On-chip cell culture technology is a technology that may increase the physiological similarity of cells by culturing cells in a microchip that has an environment similar to the internal environment of living bodies including the human body. For example, intestinal uptake and hepatic metabolism of the human body may be simulated closely by culturing intestinal cells and liver cells in completed chips.

A recent report says that the activity and function of cells are improved when, without culturing the cells in a plastic dish, the cells are cultured in a microfluidic chip that simulates the blood flow and intestinal fluid flow of an actual human body. Accordingly, there is a growing need for cell culture chips, which are cell culture systems including fluid flow.

Currently, studies on three-dimensional cell culture and organs-on-a-chip have been conducted. However, since only a limited function of a single organ model is simulated, it is difficult to form multiple organ networks on a single chip, and the interaction between organs in the human body may not be simulated. For this reason, it is essential to optimize the conditions for culturing various organs together after forming multiple organ networks in vitro. However, due to the absence of a device capable of simulating a biological environment similar to an actual biological condition, it is difficult to conduct the related research. In particular, in the case of brain research, it is difficult to conduct in vitro experiments in which various brain region connections are formed in vitro and the influence of other brain regions connected upon selective external stimulation for a specific brain region is identified.

In addition, the structures of chips capable of culturing two or more organs vary depending on an organ to be simulated and are complicated, and the chips need to be connected to an external system, such as an external pump, tubing, or wires. Accordingly, the compatibility of the chips with existing experimental equipment is low and it is difficult to implement a high-speed mass processing system. In addition, cell culture devices of the related art include only non-exposure models as culture models, and unlike the flow of blood or body fluid in an actual living body, the flow of the culture fluid in the device is bi-directional.

Lastly, in the case of organs-on-a-chip of the related art, cells are attached to the surface of a chip inside the chip and cultured, and thus it is not possible to collect the cells from the chip for further analysis.

SUMMARY

An aspect of the present disclosure is to provide a biomimetic chip device that simulates a biological environment including a human body.

Additional aspects will be set forth in part in the description which follows and, in part, will be apparent from the description, or may be learned by practice of the presented embodiments of the disclosure.

An aspect of the present disclosure provides a biomimetic chip device including a body, a main channel arranged in the body and extending in one direction, a plurality of culture chambers spaced apart from each other on the main channel, a first reservoir arranged at one end of the main channel and storing a first fluid, a second reservoir arranged at the other end of the main channel and storing the first fluid, wherein the body is tilted about a first axis perpendicular to the one direction to allow the first fluid to flow between the first reservoir and the second reservoir.

In one or more embodiments, in the biomimetic chip device, a plurality of culture models may be cultured in the culture chambers, wherein the plurality of culture models are arranged in the one direction according to the order in which blood is supplied in a living body.

In one or more embodiments, in the biomimetic chip device, the culture models may include a non-exposure model of the inside of the living body and an exposure model of the outside of the living body, and the first fluid flows from the first reservoir to the second reservoir through the culture chambers culturing the non-exposure model and the exposure model.

In one or more embodiments, the biomimetic chip device may further include a bypass channel arranged in parallel with the main channel to return, to the first reservoir, the first fluid which has moved from the first reservoir to the second reservoir.

In one or more embodiments, when the body is tilted in a first direction, the first fluid moves along the main channel, and when the body is tilted in a second direction opposite to the first direction, the first fluid moves along the bypass channel.

In one or more embodiments, the biomimetic chip device may further include a first valve unit arranged at both ends of the main channel; and a second valve unit arranged at both ends of the bypass channel.

In one or more embodiments, each of the first valve unit and the second valve unit may be a ball valve for moving the first fluid in a pre-set flow direction.

In one or more embodiments, the biomimetic chip device further includes a sub-channel through which the second fluid moves, a portion of the sub-channel being arranged in parallel with the bypass channel, wherein the first fluid moving through the bypass channel exchanges material with the second fluid moving through the sub-channel.

In one or more embodiments, the biomimetic chip device may further include a membrane between the bypass channel and the sub-channel.

In one or more embodiments, in the biomimetic chip device, in the bypass channel and the sub-channel, the first fluid and the second fluid exchange materials when the body rotates in a pre-set direction.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 6 is a diagram illustrating a biomimetic chip device including a sub-channel and a membrane, according to another embodiment;

DETAILED DESCRIPTION

Figure 1:
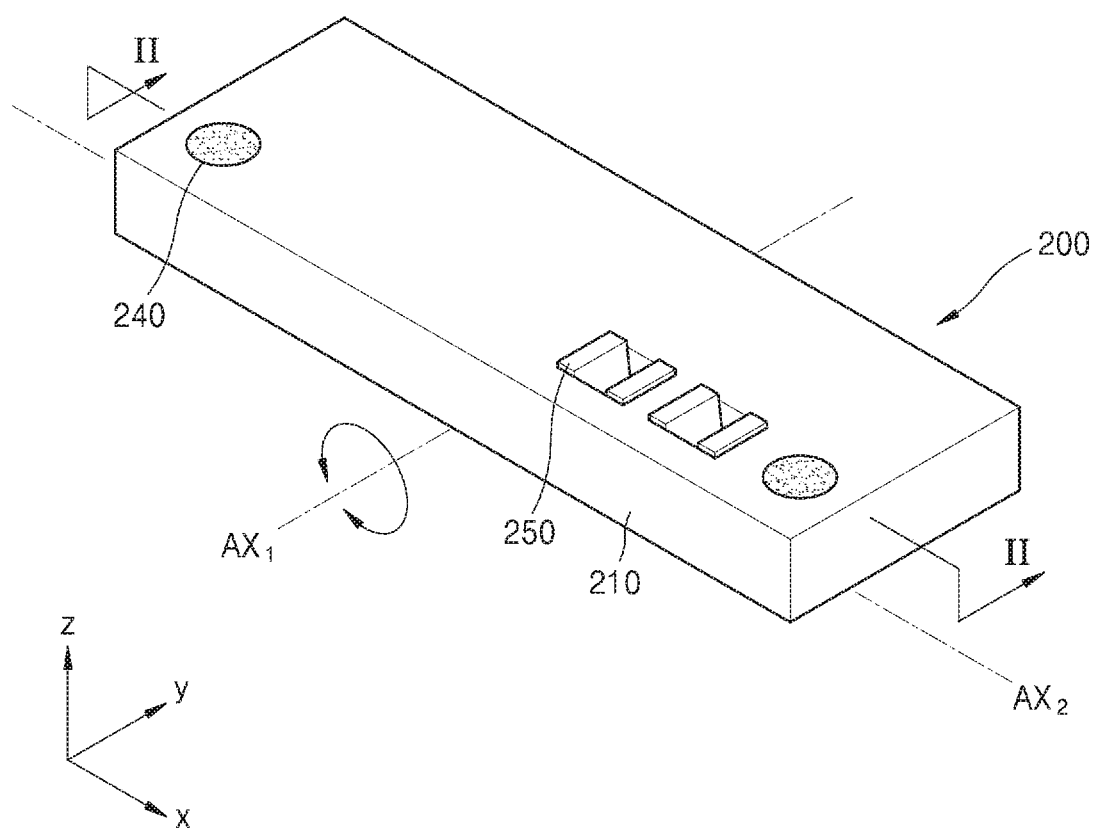
FIG. 1 is a diagram illustrating a biomimetic chip device according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that, although the terms first, second, etc. may be used herein to describe various elements, these elements should not be limited by these terms. The terms are only used to distinguish one element from another.

The terminology used herein is for the purpose of describing particular example embodiments only and is not intended to be limiting of present disclosure. In the present application, the terms "comprises" or "having" are intended to specify the presence of stated features, integers, steps, operations, elements, components, or combinations thereof, but do not preclude the presence or addition of one or more other features, integers, steps, operations, elements, components, or combinations thereof.

Hereinafter, the present disclosure will be described in detail with reference to embodiments of the present disclosure shown in the accompanying drawings.

Figure 2:
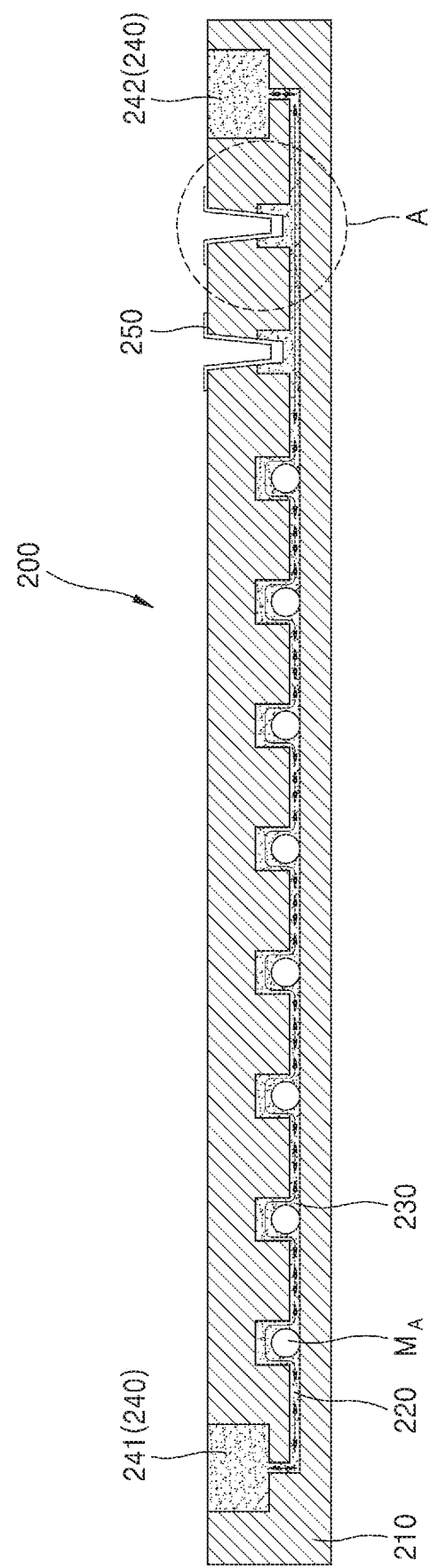
FIG. 2 is a diagram illustrating a cross-section of a biomimetic chip device taken along line II-II of FIG. 1.

FIG. 1 is a diagram illustrating a biomimetic chip device 200 according to an embodiment of the present disclosure, and FIG. 2 is a diagram illustrating a cross-section of the biomimetic chip device 200 taken along line II-II of FIG. 1.

Referring to FIGS. 1 and 2, the biomimetic chip device 200 according to an embodiment of the present disclosure includes a body 210, a main channel 220 provided in the body 210 and extending in one direction, a plurality of culture chambers 230 spaced apart from each other on the main channel 220, a first reservoir 241 arranged at one end of the main channel 220 and storing a first fluid, and a second reservoir 242 arranged at the other main channel 220 and storing the first fluid, wherein the body 210 is tilted about a first axis that is perpendicular to one direction to enable the first fluid to flow between the first reservoir 241 and the second reservoir 242.

The body 210 forms the basic shape of the biomimetic chip device 200, and other members may be arranged therein. The shape of the body 210 is not particularly limited, and, in an embodiment of the present disclosure, the shape of the body 210 may be a rectangular parallelepiped shape extending in one direction. In one embodiment, the body 210 may include a transparent material to easily observe the inside of the body 210 from the outside. A member for tilting the biomimetic chip device 200 may be coupled to one side of the body 210.

FIG. 2, the main channel 220 is arranged in the body 210 and extends in one direction. The main channel 220 is arranged inside the body 210 to provide an internal flow path through which the first fluid moves. As described later, one end of the main channel 220 is connected to the first reservoir 241 and the other end thereof is connected to the second reservoir 242. In an embodiment of the present disclosure, the main channel 220 may be arranged in an X-axis direction (the longitudinal direction of the biomimetic chip device 200) such that the main channel 220 is parallel to the bottom surface of the body 210.

The first fluid is a fluid required for culturing and growing a culture model M. In the embodiment of the present disclosure, the first fluid may be a culture medium that supplies oxygen and nutrients to the culture model M.

In an embodiment of the present disclosure, the culture model M is a model corresponding to a specific part of the living body, and may include a non-exposure model $M_A$ inside the living body and an exposure model $M_B$ outside the living body. The non-exposure model $M_A$ may include models for non-exposed organs such as liver, tumor, heart, and the like. The exposure model $M_B$ may include a model for exposed organs such as skin, nasal cells, and the like.

The plurality of culture chambers 230 are arranged on the main channel 220. In each of the culture chambers 230, a culture model is arranged and incubated. The numbers of the culture chambers 230 and the culture models M are not particularly limited, and appropriate numbers thereof may be used in consideration of characteristics of the culture model M and the purpose of the experiment.

In another embodiment, culture models M may be arranged in one direction according to the order in which blood is supplied in the living body. For example, the blood in the body flows in the order of brain, heart, liver, tumor, skin, nasal cavity, and flows from the inner center of the body toward the periphery. In consideration of the order described above, culture models M may be arranged in the culture chambers 230 in the order of the non-exposure model $M_A$ and the exposure model $M_B$ from the first reservoir 241 to the second reservoir 242. In addition, non-exposure models $M_A$ may be arranged in the order of the brain model, the heart model, the liver model, the tumor model, and exposure models $M_B$ may be arranged in order of the skin model and the nasal model. Thus, the first fluid is supplied from the first reservoir 241, and flows, through the non-exposure model ($M_A$) and the exposure model ($M_B$) in the main channel 220 in the order of the blood supply in the living body, to the second reservoir 242. Through this configuration, it is possible to implement a culturing environment in which the flow of blood in the actual living body is considered.

The non-exposure model $M_A$ may be arranged in the culture chamber 230 in the form of a spheroid as a three-dimensional organoid. Accordingly, the non-exposure model $M_A$ is incubated while staying inside the culture chamber 230 and maintaining a three-dimensional shape thereof, without being adsorbed on the inner surface of the culture chamber 230. Therefore, the non-exposure model $M_A$ may be recovered to the outside of the device after incubation for further analysis. The exposure model $M_B$ may be arranged in the culture chamber 230 via a culture unit 250. This will be described in more detail with reference to FIG. 3.

Figure 3:
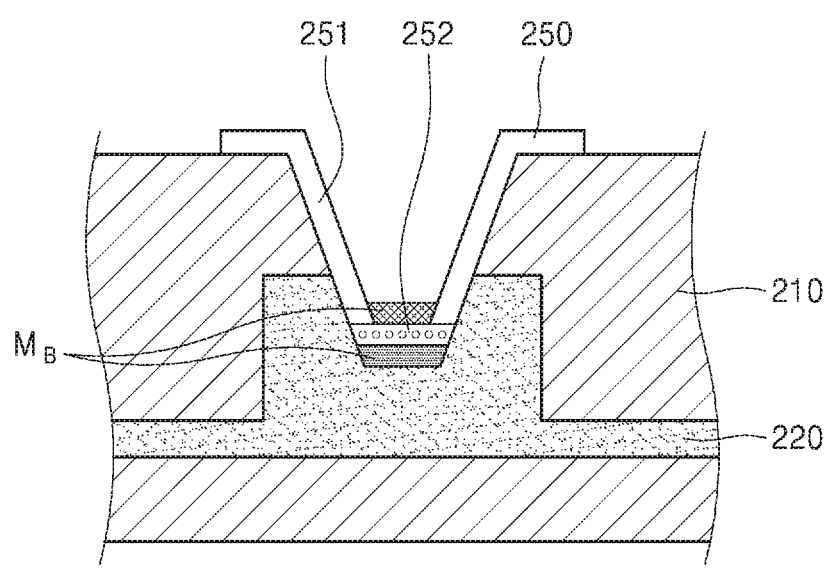
FIG. 3 is an enlarged view of region A of FIG. 2.

FIG. 3 is an enlarged view of A of FIG. 2.

Referring to FIGS. 2 and 3, the exposure model $M_B$ may be arranged at the culture unit 250 and inserted into the culture chambers 230 through a groove formed on the top surface of the body 210. The culture unit 250 is detachable with respect to the biomimetic chip device 200, and includes a guide portion 251 and a bottom membrane 252.

The guide portion 251 is a member having a V-shape whose upper end is bent outward when viewed from the front. The bent portion of the guide portion 251 is supported on the top surface of the body 210, and the sidewall of the guide portion 251 is supported on the sidewall of a groove (not shown) formed at the top surface of the body 210. The bottom membrane 252 may constitute the bottom end of the guide portion 251 The bottom membrane 252 is a membrane capable of exchanging material with the outside, and from among the exposure model $M_B$, exposure cells may be arranged above the bottom membrane 252 and vascular endothelial cells may be arranged beneath the bottom membrane 252.

As such, the exposure model $M_B$ may be arranged in the culture unit 250 outside the biomimetic chip device 200 and then inserted into the culture chamber 230. The culture unit 250 may be a transwell.

That is, in an embodiment of the present disclosure, the biomimetic chip device 200 may modulate a culture model by placing the non-exposure model $M_A$ in the spheroid form in the culture chamber 230, and the exposure model $M_B$ in the culture unit 250. Accordingly, the culture model may be easily taken out of the biomimetic chip device 200 during the culture process or after the culture process is completed, and further analysis may be performed the outside the biomimetic chip device 200.

In one or more embodiments, the biomimetic chip device 200 may further include a loading channel (not shown) and a loading chamber (not shown) to place the non-exposure model $M_A$ into the culture chamber 230. For example, like a loading channel 370 and a loading chamber 380 of a biomimetic chip device 300 shown in FIGS. 8 and 9, the body 210 may include a loading chamber and a loading channel on one side thereof, wherein the non-exposure model $M_A$ is arranged in the loading chamber, and the loading channel extends from the loading chamber and is connected to the culture chambers 230. Accordingly, as the body 210 is tilted about a second axis parallel to a direction in which the main channel 220 extends (for example, axis $AX_2$ of FIG. 1), the non-exposure model $M_A$ in the loading chamber may be loaded into the culture chamber 230 via the loading channel.

In one or more embodiments, an inlet for seating the non-exposure model $M_A$ in the culture chamber 230 may be formed directly on the culture chamber 230. For example, like the reservoir 240, the culture chamber 230 has an open top surface, allowing the non-exposure model MA to be seated directly into the culture chamber 230. In this case, the biomimetic chip device 200 may not have a loading channel and a loading chamber, and thus may have a simple structure. In one or more embodiments, the biomimetic chip device 200 may further include a cover (not shown) for opening and closing the open top surface of the culture chamber 230.

Referring to FIGS. 1 and 2, the reservoir 240 is a member for storing and supplying the first fluid, and may include the first reservoir 241 and the second reservoir 242. The first reservoir 241 is arranged on one side of the top surface of the body 210 and the second reservoir 242 is arranged on the other side of the top surface of the body 210. In an embodiment of the present disclosure, the first reservoir 241 and the second reservoir 242 may be inserted into the body 210 through a groove (not shown) formed on the top surface of the body 210.

The first reservoir 241 is connected to one end of the main channel 220 and the second reservoir 242 is connected to the other end of the main channel 220. The first reservoir 241 and the second reservoir 242 may each have an internal space for storing the first fluid therein. The first reservoir 241 and the second reservoir 242 may each have various shapes, and may have a cylindrical shape or a downwardly tapered shape. In an embodiment of the present disclosure, the first reservoir 241 and the second reservoir 242 may each have a cylindrical shape having an internal space. In addition, the first reservoir 241 and the second reservoir 242 may have an open top surface to supply the first fluid from the outside.

In one or more embodiments, the biomimetic chip device 200 may optionally include a cover (not shown) to open and close the top surface of the reservoir 240. Accordingly, even when the biomimetic chip device 200 is tilted, the first fluid may be prevented from being separated from the reservoir 240.

Figure 4:
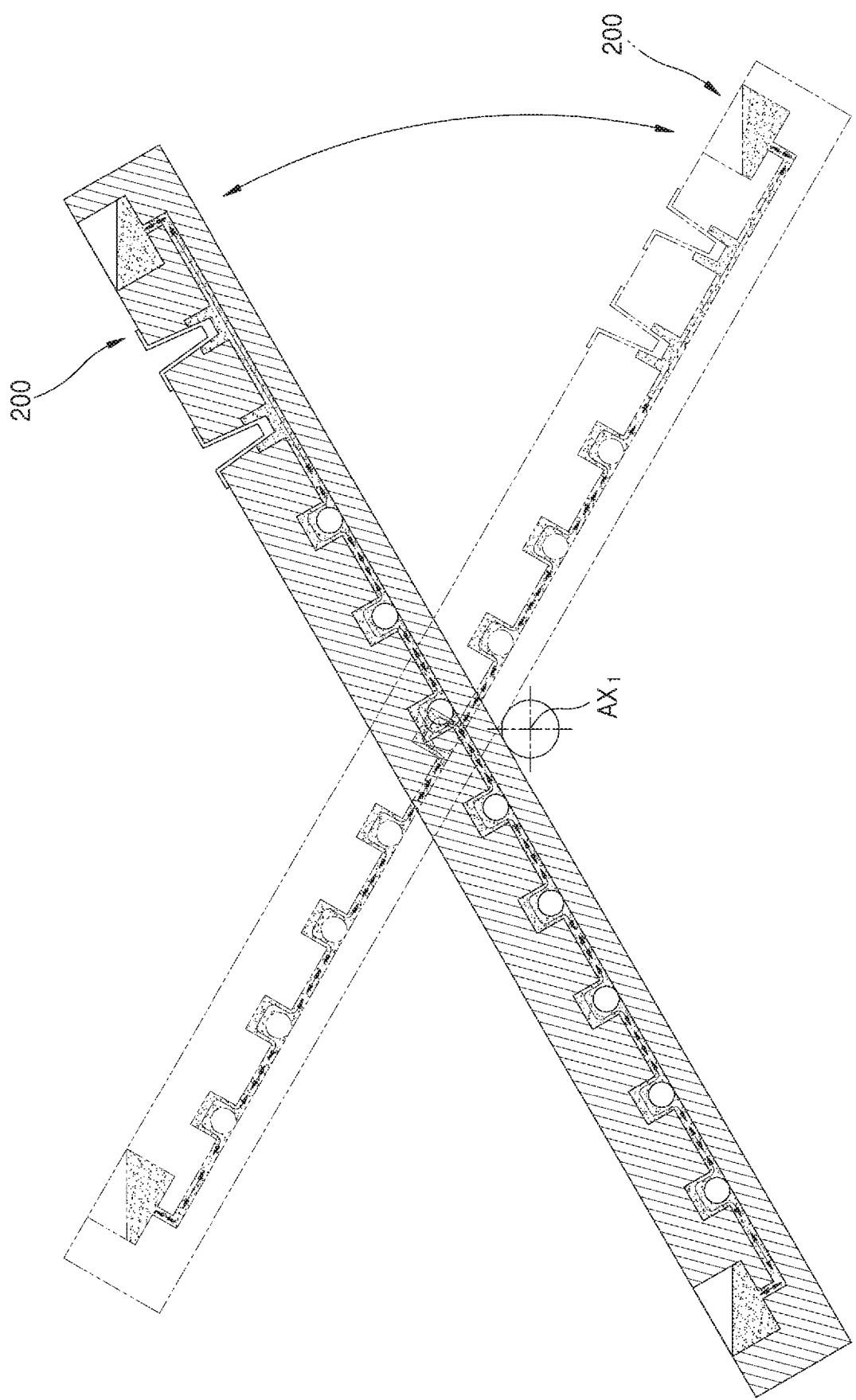
FIG. 4 shows that a biomimetic chip device is tilted about axis $AX_1$.

FIG. 4 is a diagram illustrating that the biomimetic chip device 200 is tilted about axis $AX_1$.

Referring to FIGS. 1, 2, and 4, axis $AX_1$ may be arranged parallel to the Y axis at the center of the X-axis direction of the biomimetic chip device 200. As shown in FIG. 4, when the biomimetic chip device 200 is tilted clockwise about axis $AX_1$, the first fluid is provided from the first reservoir 241 to each of the culture chambers 230 through the main channel 220. The first fluid which has passed through the culture chambers 230, moves to the second reservoir 242. Conversely, when the biomimetic chip device 200 is tilted counterclockwise about axis $AX_1$, the first fluid moves from the second reservoir 242 to the first reservoir 241.

In addition, as described above, the biomimetic chip device 200 may further include a loading channel and a loading chamber which are provided to seat the non-exposure model $M_A$ in the culture chamber 230. In this case, the body 210 may be tilted about axis $AX_2$ to move the non-exposure model $M_A$ injected into the loading chamber to the culture chamber 230. Referring to FIG. 1, in an embodiment of the present disclosure, axis $AX_2$ may be arranged on the bottom surface of the body 210 and below the culture model M.

As such, the biomimetic chip device 200 according to the present disclosure may simply form a fluid flow by tilting the body 210 based on gravity, without the inclusion of a pump, a microtubule, or a tubing, thereby reducing the size and weight thereof.

On the other hand, the sizes of the exposure model $M_A$ and the non-exposure model $M_B$ may be greater than the size of the inner flow path of the main channel 220. Accordingly, even when the biomimetic chip device 200 is tilted, the exposure model $M_A$ and the non-exposure model $M_B$ may not move from their own culture chambers to other culture chambers. That is, each exposure model $M_A$ and each non-exposure model $M_B$ may be cultured as being spatially separated from other exposure models $M_A$ and other non-exposure models $M_B$.

Figure 5A:
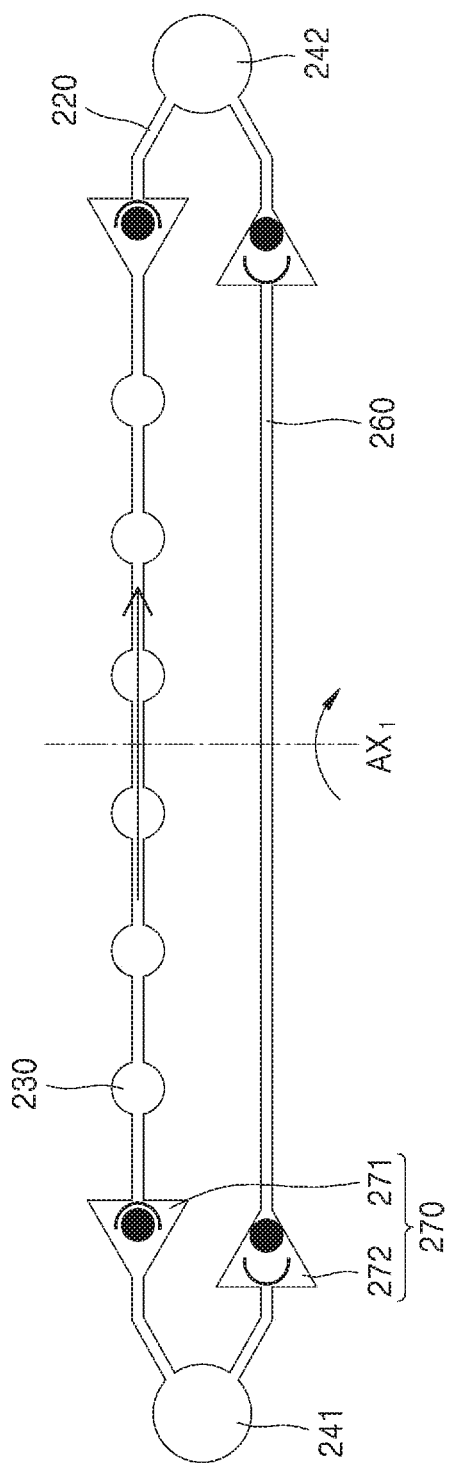
FIG. 5A is a diagram illustrating a biomimetic chip device having a bypass channel and a valve unit, according to another embodiment.
Figure 5B:
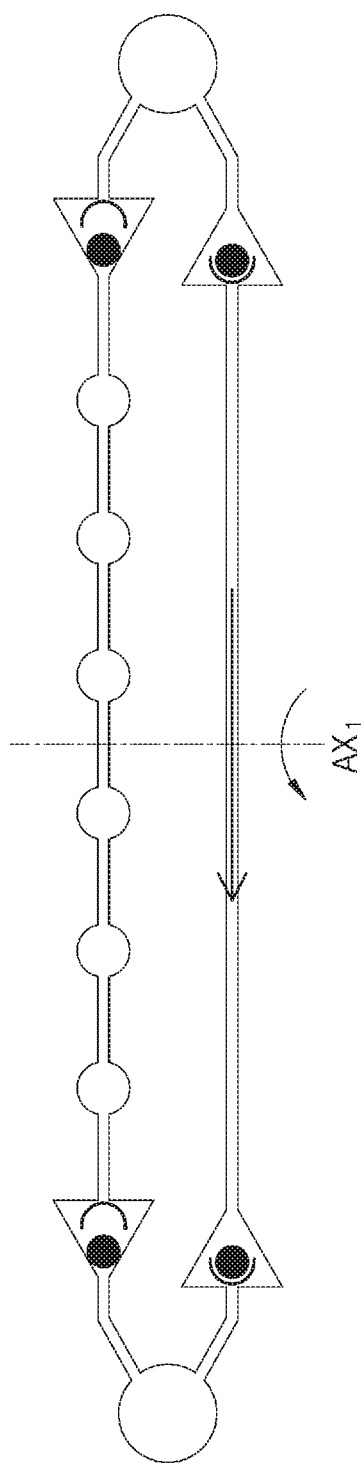
FIG. 5B is a diagram illustrating a biomimetic chip device having a bypass channel and a valve unit, according to another embodiment.

FIGS. 5A and 5B show an example of the biomimetic chip device 200 including a bypass channel 260 and a valve unit 270. FIG. 5A shows an embodiment in which the first fluid flows in the main channel 220, and FIG. 5B shows an embodiment in which the first fluid flows in the bypass channel 260.

Referring to FIGS. 5A and 5B, the biomimetic chip device 200 according to present disclosure may further include the bypass channel 260. The bypass channel 260 is arranged in parallel with the main channel 220 of the body 210, and has an end which is connected to the first reservoir 241 and the other end which is connected to the second reservoir 242. The bypass channel 260 returns, back to the first reservoir 241, the first fluid which has moved from the first reservoir 241 to the second reservoir 242.

In addition, referring to FIGS. 5A and 5B, the biomimetic chip device 200 according to the present disclosure may further include the valve unit 270. The valve unit 270 is a member that allows the fluid to flow only in a certain direction, and controls the first fluid flowing through the main channel 220 and the bypass channel 260. The valve unit 270 may be arranged in each of the main channel 220 and the bypass channel 260.

The valve unit 270 may include a first valve unit 271 and a second valve unit 272. The first valve unit 271 is arranged at one side and the other side of the main channel 220 and controls the flow of the first fluid from the first reservoir 241 to the second reservoir 242. The second valve unit 272 is arranged at one side and the other side of the bypass channel 260 and controls the flow of the first fluid from the second reservoir 242 to the first reservoir 241.

In one or more embodiments, as shown in FIG. 5A, when the biomimetic chip device 200 is tilted clockwise about axis $AX_1$, the first fluid flows from the first reservoir 241 to the second reservoir 242. The flow of the first fluid is to supply oxygen and nutrients to the culture chambers 230 arranged on the main channel 220, and in this case, the first fluid passes through the main channel 220. Thus, the first valve unit 271 is opened and the second valve unit 272 is closed. Accordingly, the first fluid flows inside the main channel 220 from the first reservoir 241 to the second reservoir 242 and does not flow inside the bypass channel 260.

In contrast, as shown in FIG. 5B, when the biomimetic chip device 200 is tilted counterclockwise about axis $AX_1$, the flow of first fluid from the second reservoir 242 to the first reservoir 241 occurs. The flow of the first fluid occurring in this case is to recover the first fluid supplied to the culture chambers 230 and the first fluid passes through the bypass channel 260. Thus, the first valve unit 271 is closed and the second valve unit 272 is opened. Accordingly, the first fluid flows inside the bypass channel 260 from the second reservoir 242 to the first reservoir 241 and does not flow inside the main channel 220.

As described above, the configuration of the valve unit 270 is not limited as long as the flow of the first fluid is selectively controlled. In an embodiment of the present disclosure the valve unit 270 may be a ball valve including a ball and a ball support. Accordingly, in the case in which the biomimetic chip device 200 is tilted about axis $AX_1$, as shown in FIG. 5A, when the ball is separated from the ball support and thus the main channel 220 or the bypass channel 260 is closed, the flow of the first fluid may be blocked. On the contrary, as shown in FIG. 5B, when the ball is seated on the ball support and the main channel 220 or the bypass channel 260 is opened, the first fluid may be allowed to flow.

As such, the biomimetic chip device 200 according to the present disclosure may be configured such that the first fluid flows only in one of the main channel 220 and the bypass channel 260, that is, the first fluid flows in only one direction. Through this configuration, it is possible to implement a culturing environment similar to the actual biological environment in which blood is supplied only in one direction.

Figure 7:
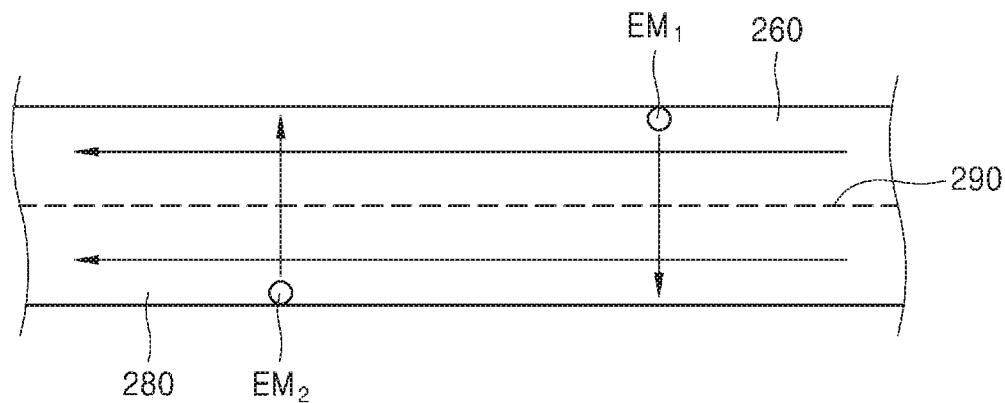
FIG. 7 is an enlarged view of region B of FIG. 6.

FIG. 6 shows an example of the biomimetic chip device 200 including a sub-channel 280 and a membrane 290, and FIG. 7 is an enlarged view of portion B of FIG. 6.

Referring to FIGS. 6 and 7, the biomimetic chip device 200 may further include the sub-channel 280. Both ends of the sub-channel 280 may be respectively connected to additional reservoirs R, and a portion of the sub-channel 280 may be arranged in parallel with the bypass channel 260. In addition, a material-exchange may occur in a section in which the bypass channel 260 and the sub-channel 280 are arranged in parallel to each other.

In detail, the biomimetic chip device 200 may further include a membrane 290 between the bypass channel 260 and the sub-channel 280. The membrane 290 is arranged at the boundary surface of the bypass channel 260 and the sub-channel 280, inducing material exchange between the bypass channel 260 and the sub-channel 280.

For example, the first fluid, supplied from the first reservoir 241 to the second reservoir 242 through the culture chambers 230, supplies oxygen and nutrients to each of the culture models M and receives waste products therefrom. Therefore, the first fluid moved to the second reservoir 242 may not be reused. In this case, a second fluid supplied from the additional reservoir R, while flowing through the sub-channel 280, may selectively perform material exchange with the bypass channel 260 through the membrane 290 according to the concentration difference and the size of the material and the size of the pores inside a membrane.

In one or more embodiments, as the body 210 is tilted, the first fluid moves from the second reservoir 242 to the first reservoir 241, and the second fluid also moves between the additional reservoirs R in the same direction as the direction in which the first fluid moves. In this case, the waste contained in the first fluid may move to the second fluid through the membrane 290 ($EM_1$), and oxygen and nutrients contained in the second fluid may move to the first fluid ($EM_2$). The second fluid which has supplied oxygen and nutrients and received the waste, is recovered to the additional reservoir R. Then, by analyzing the recovered waste, the culture state of the culture model M may be monitored.

In one or more embodiments, the membrane 290 may include a plurality of layers. In detail, the membrane 290 may include a first membrane arranged on the bypass channel 260 and a second membrane arranged on the sub-channel 280.

In one or more embodiments, the material exchange between the bypass channel 260 and the sub-channel 280 may be set to occur only when the body 210 is tilted in a specific direction. In one or more embodiments, the material exchange between the bypass channel 260 and the sub-channel 280 may be set to occur only when the body 210 is tilted counterclockwise about axis $AX_1$ so that the first fluid flows through the bypass channel 260 and the second fluid also flows through the sub-channel 280 in the same direction as the direction in which the first fluid flows. In this case, the valve unit 270 may be arranged at both ends of the sub-channel 280.

As such, due to the inclusion of the membrane 290, the biomimetic chip device 200 may implement a simple kidney function for selectively separating specific materials between the flows of fluids.

In one or more embodiments, the main channel 220, the culture chamber 230 and the reservoir 240 may be arranged in a plurality of rows. In one or more embodiments, the biomimetic chip device 200 according to the present disclosure may be configured to correspond to a standard 96 well micro plate format. As a result, the compatibility with existing cell culture automation equipment may be increased, and thus, high-speed mass screening may be put into practical use.

Figure 8:
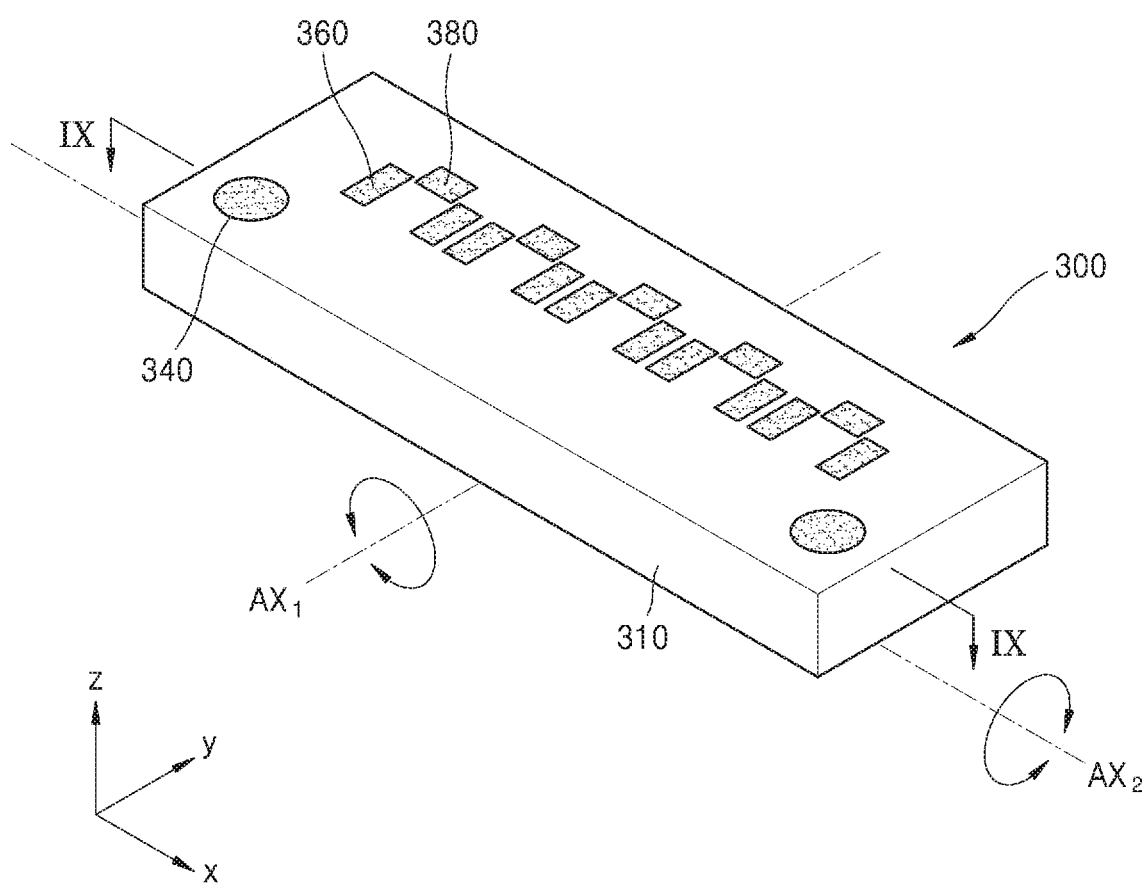
FIG. 8 is a diagram illustrating a biomimetic chip device according to another embodiment.
Figure 9:
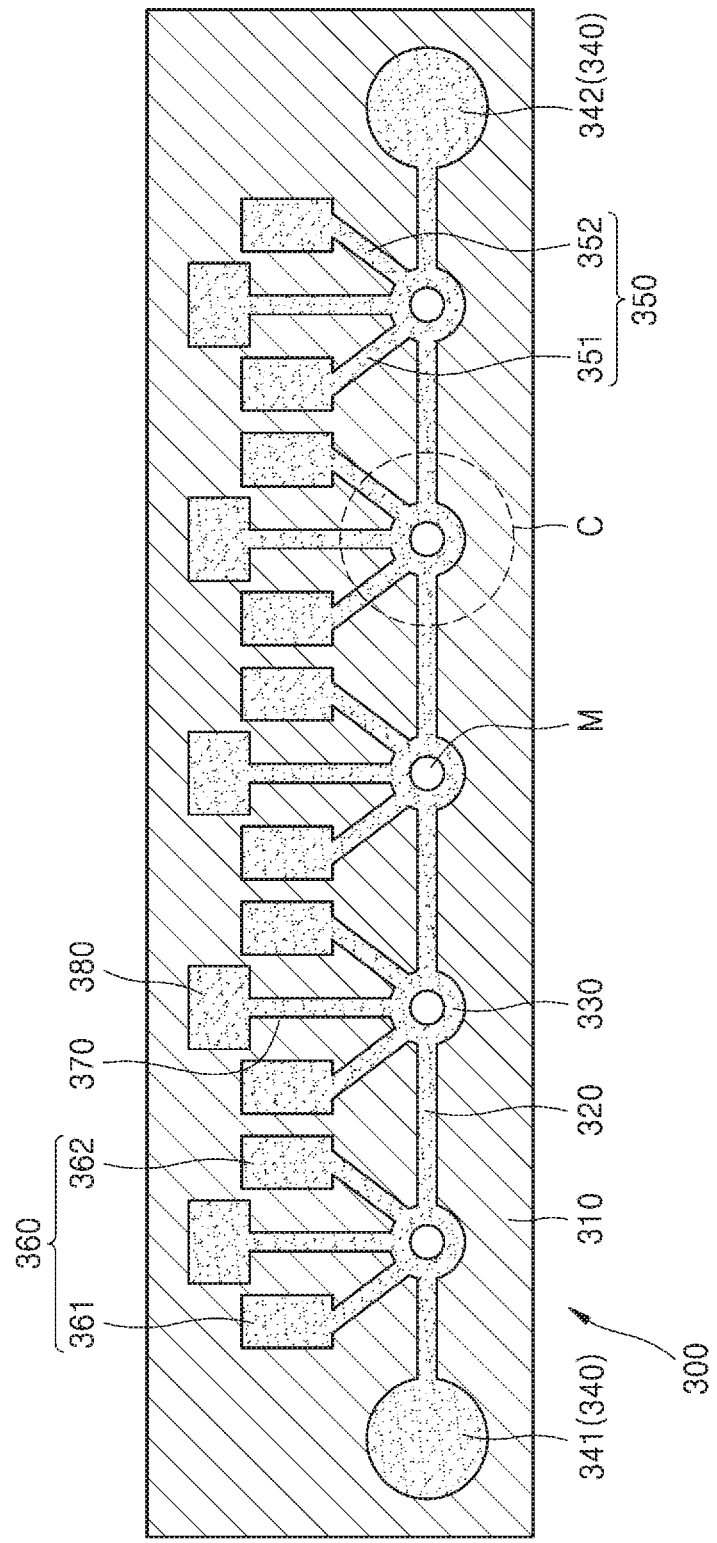
FIG. 9 is a diagram illustrating a cross-section of the biomimetic chip device taken along line VIII-VIII of FIG. 8.

FIG. 8 is a diagram illustrating a biomimetic chip device 300 according to another embodiment of present disclosure, and FIG. 9 is a diagram illustrating a cross-section of the biomimetic chip device 300 taken along the line VIII-VIII of FIG. 8.

Referring to FIGS. 8 and 9, the biomimetic chip device 300 according to another embodiment of present disclosure includes a body 310, a main channel 320 arranged in the body 310 and extending in one direction, a plurality of culture chambers 330 spaced apart from each other on the main channel 320, a first reservoir 341 arranged at one end of the main channel 320 and storing a first fluid, a second reservoir 342 arranged at the other end of the main channel and storing the first fluid, a sub-channel 350 connected to at least one of the plurality of culture chambers 330 and extending in a direction different from the one direction, and an injection chamber 360 arranged at an end of the sub-channel 350 and supplying a second fluid to the culture chamber 330 through the sub-channel 350.

The body 310 forms the basic shape of the biomimetic chip device 300, and other members may be arranged therein. The body 310 may be the same as the body 210 of the biomimetic chip device 200 according to the previous embodiment of the present disclosure, and a detailed description thereof will be omitted.

FIG. 9, the main channel 320 is arranged in the body 310 and extends in one direction. The main channel 320 is arranged inside the body 310 to provide an internal flow path through which the first fluid moves. One end of the main channel 320 is connected to the first reservoir 341 and the other end thereof is connected to the second reservoir 342. In an embodiment of the present disclosure, the main channel 320 may be arranged inside the body 310 and may extend in the X-axis direction (the longitudinal direction of the biomimetic chip device 300) to be parallel to the bottom surface of the body 310. For example, the main channel 320 may include a fine channel array having a width and height of 3 μm to 5 μm to guide the direction in which neurites of brain models, which are used as the culture model M, grow and to promote the growth the neurites.

The first fluid is a fluid required for culturing and growing a culture model M. In the embodiment of the present disclosure, the first fluid may be a culture medium that supplies oxygen and nutrients to the culture model M.

The culture model M is not particularly limited and may be a model corresponding to a specific part of the living body. In an embodiment of the present disclosure, the culture model M may be a three-dimensional brain organoid model including neurons obtained from different brain regions.

The culture chambers 330 may each be a member having an internal space in which the culture model M is cultured. The culture chambers 330 may be arranged on the main channel 320, and the culture model M may be arranged and cultured in each of the culture chambers 330. The numbers of the culture chambers 330 and the culture models M are not particularly limited, and appropriate numbers thereof may be used in consideration of characteristics of the culture model M and the purpose of the experiment.

A reservoir 340 may include the first reservoir 341 and the second reservoir 342 as members for storing and supplying the first fluid. The first reservoir 341 and the second reservoir 342 may be the same as the first reservoir 241 and the second reservoir 242 of the biomimetic chip device 200 according to the embodiment of the present disclosure described above, a detailed description thereof will be omitted.

The flow of the first fluid may be generated by tilting the body 310. For example, when the body 310 is tilted about a first axis perpendicular to one direction (e.g., axis AXE of FIG. 8) in which the main channel 320 extends, the flow of the first fluid may occur inside the first reservoir 341, the second reservoir 342, and the main channel 320 connecting the first reservoir 341 and the second reservoir 342 each other.

The sub-channel 350 is connected to the culture chambers 330 and arranged inside the body 310 to provide an internal flow path through which the second fluid moves. The sub-channel 350 may include a first injection tube 351 and a second injection tube 352. The first injection tube 351 and the second injection tube 352 each extend from the culture chambers 330, and may be arranged to be symmetrical to each other. In an embodiment of the present disclosure, the first injection tube 351 and the second injection tube 352 may be arranged in a V shape around the culture chambers 330.

The sub-channel 350 may be arranged on the same plane as the main channel 320. The sub-channel 350 may be provided for all of the culture chambers 330 or may be selectively provided for some of the culture chambers 330 which need to be supplied with the second fluid.

In one or more embodiments, the first injection tube 351 and the second injection tube 352 of the sub-channel 350 may extend in opposite directions about the culture chambers 330. That is, the first injection tube 351 and the second injection tube 352 extend in opposite directions about the culture chambers 330, so that the sub-channel 350 and the main channel 320 may cross each other.

The second fluid may be the same as or different from the first fluid. In an embodiment of the present disclosure, the second fluid may be a drug that imparts chemical stimulation to the culture medium or the culture model M.

The injection chamber 360 is connected to the end of the sub-channel 350 and supplies the second fluid to the culture chambers 330 through the sub-channel 350. The injection chamber 360 may include the first injection portion 361 and the second injection portion 362. In an embodiment of the present disclosure, the first injection portion 361 and the second injection portion 362 may be inserted into the body 310 through grooves (not shown) formed on the top surface of the body 310. The first injection portion 361 is connected to the other end of the first injection tube 351, the second injection portion 362 is connected to the other end of the second injection tube 352, and the first injection portion 361 and the second injection portion 362 are spaced apart from each other. That is, the first injection tube 351 and the first injection portion 361 may be arranged to be symmetrical to the second injection tube 352 and the second injection portion 362, with respect to the culture chambers 330.

The first injection portion 361 and the second injection portion 362 each have an internal space for storing the second fluid therein. The first injection portion 361 and the second injection portion 362 may have various shapes, and, in the embodiment of the present disclosure, may have a tapered shape or the like. In addition, the first injection portion 361 and the second injection portion 362 may each have an open top surface to supply the second fluid from the outside.

In one or more embodiments, the injection chamber 360 may be selectively activated when the flow of the first fluid is disturbed by the culture model M in the culture chamber 330. For example, when the culture model M is a neuronal model, as the culture model M is cultured, the neurites extending from each culture model M are connected to each other, resulting in a narrow flow path of the main channel 320. Accordingly, the flow resistance of the fluid in the main channel 320 is increased so that the first fluid may not be smoothly supplied to the culture model M through the main channel 320. In this case, for the supply of the culture medium to the culture model M, the body 310 is tilted to supply the second fluid from the injection chamber 360 to the culture chamber 330. The body 310 may be tilted about the first axis (e.g., axis $AX_1$ of FIG. 8) perpendicular to a direction in which the main channel 320 extends. In this case, the second fluid may be a culture medium.

In one or more embodiments, the second fluids stored in the plurality of injection chambers 360 may be different drugs. Accordingly, a different drug may be used for the culture model M arranged in the injection chamber 360 to impart a chemical stimulus thereto.

The loading channel 370 has one end connected to the culture chamber 330 and is arranged inside the body 310 to provide an internal passage through which the culture model M may move. The loading channel 370 may extend in a direction different from a direction in which the main channel 320 extends. Accordingly, even when the body 310 is tilted to supply the first fluid, the first fluid does not leak from the main channel 320 to the loading chamber 380. In an embodiment of the present disclosure, the loading channel 370 may be arranged to be perpendicular to a direction in which the main channel 320 extends. In addition, the loading channel 370 may be arranged on the same plane as the main channel 320.

The loading chamber 380 is connected to the other end of the loading channel 370. The culture model M is injected into the loading chamber 380 from the outside and seated therein. In an embodiment of the present disclosure, the loading chamber 380 may be inserted into the body 310 through a groove (not shown) formed on the top surface of the body 310. The loading chamber 380 has an internal space in which the culture model M is seated. The loading chamber 380 may have various shapes, and an embodiment of the loading chamber 380 may have an internal space and may have a tapered shape. In addition, the loading chamber 380 may have an open top surface so that the culture model M is injected from the outside.

The culture model M of the loading chamber 380 may be loaded into the culture chambers 330 via the loading channel 370, when the body 310 is tilted. In one or more embodiments, when the body 310 is tilted about a second axis parallel to a direction in which the main channel 320 extends (e.g., axis $AX_2$ of FIG. 1), the culture model M in the loading chamber 380 may be loaded into the culture chambers 330 through the loading channel 370.

In one or more embodiments, the biomimetic chip device 300 may optionally include a cover (not shown) for opening and closing the top surface of each of the reservoir 340, the injection chamber 360 and the loading chamber 380. Accordingly, even when the biomimetic chip device 300 is tilted, since the reservoir 340, the injection chamber 360, and the loading chamber 380 are covered by the cover, the separation of the first fluid, the second fluid, or the culture model M from the reservoir 340, the injection chamber 360, and the loading chamber 380 may be prevented.

In one or more embodiments, the culture model M may be introduced directly into the culture chambers 330 without passing through the loading channel 370 and the loading chamber 380. For example, like the reservoir 340, each of the culture chambers 330 has an open top surface, allowing the culture model M to be seated directly into the culture chambers 330. In this case, the biomimetic chip device 300 may have a simple structure due to the absence of the loading channel 370 and the loading chamber 380. In one or more embodiments, the biomimetic chip device 300 may further include a cover (not shown) for opening and closing the open top surface of each of the culture chambers 330.

In one or more embodiments, the body 310 may be formed by combining a plurality of members. For example, the body 310 may be separated into a lower body and an upper body, and after other members are arranged on the lower body, the upper body may be arranged thereon to cover the same. Accordingly, the culture model M may be observed by separating only the upper body from the lower body, or the culture model M may be taken out from the biomimetic chip device 300.

In one or more embodiments, the main channel 320, the sub-channel 350 and the loading channel 370 may be arranged to be inclined with respect to the bottom surface of the body 310. For example, the loading channel 370 may be arranged to be inclined downward toward the culture chambers 330. Accordingly, when the culture model M is injected into the loading chamber 380, the culture model M may naturally move to the culture chambers 330 along the loading channel 370 to be seated.

Figure 10:
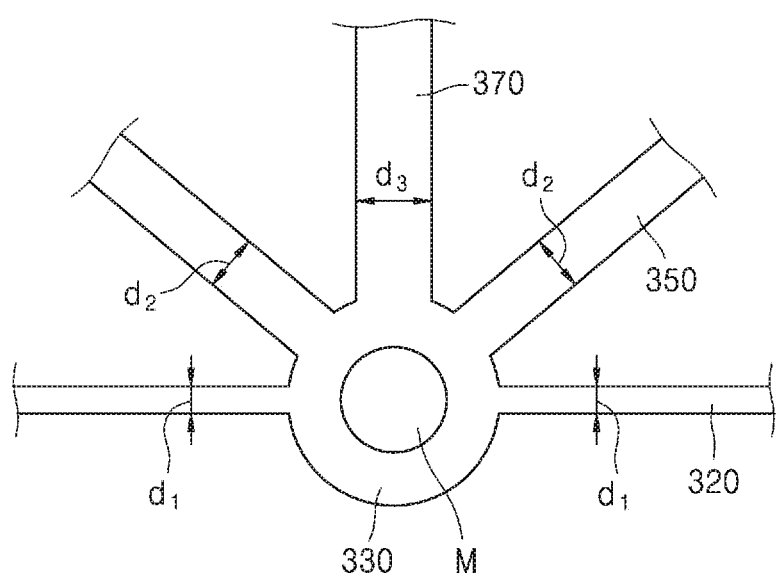
FIG. 10 is an enlarged view of region C of FIG. 9.

FIG. 10 is an enlarged view of C of FIG. 9.

As described above, the main channel 320 extends in one direction in the body 310, and the culture chambers 330 are arranged on the main channel 320. The culture model M is arranged and cultured in the culture chambers 330. The sub-channel 350 is connected to the culture chambers 330 and is arranged in a V-shape around the culture chambers 330. The loading channel 370 extends from the main channel 320 in a direction different from a direction in which the main channel 320 extends.

In one or more embodiments, diameter $d_1$ of the main channel 320 and diameter $d_2$ of the sub-channel 350 may satisfy the condition of $d_1 < d_2$. Accordingly, the hydrodynamic pressure of the first fluid flowing through the main channel 320 may be greater than the hydraulic pressure of the second fluid flowing through the sub-channel 350.

Hereinafter, the operation of the biomimetic chip device 300 according to an embodiment of the present disclosure will be described with reference to FIGS. 8 to 12.

Figure 11:
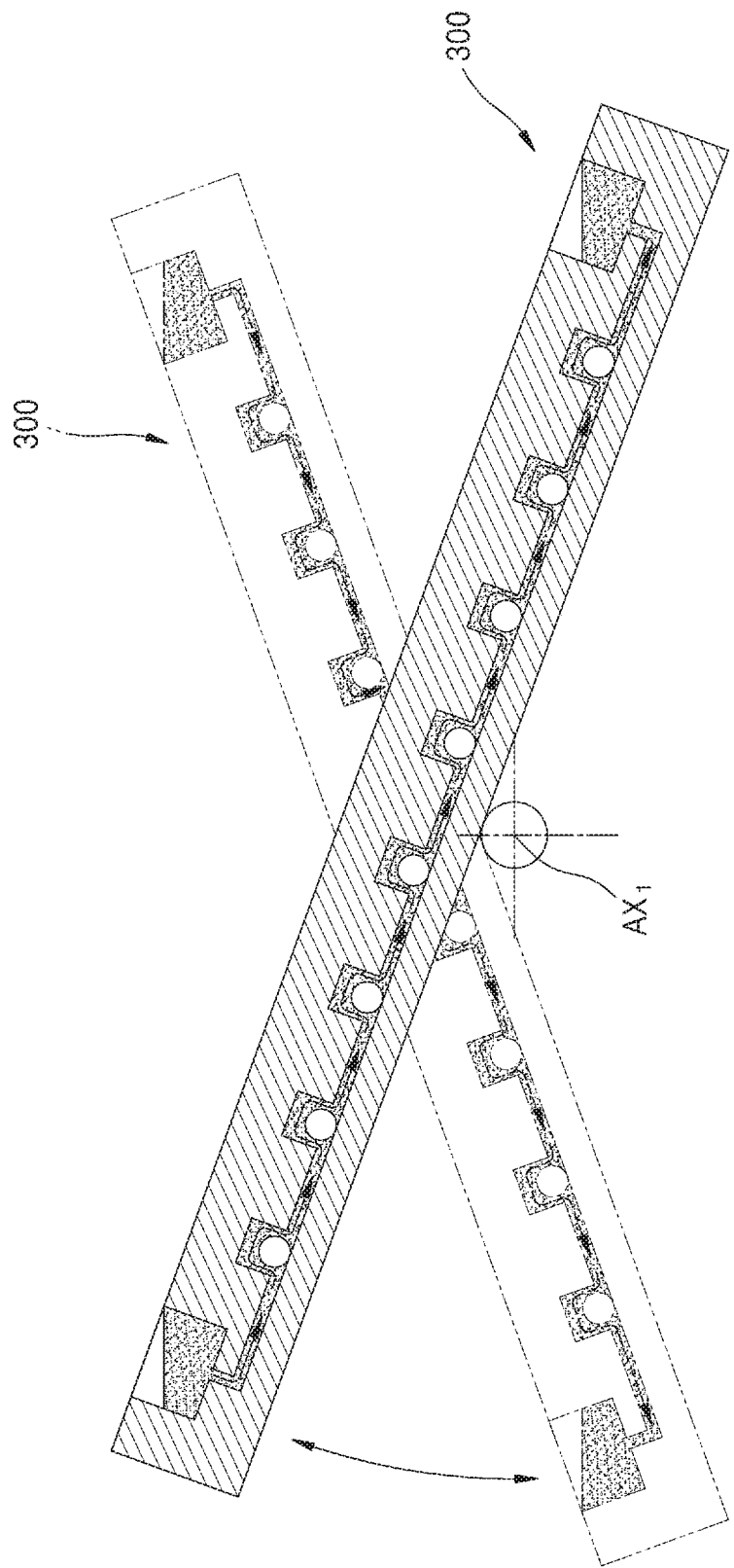
FIG. 11 is a diagram illustrating that the biomimetic chip device of FIG. 8 is tilted about axis $AX_1$.
Figure 12:
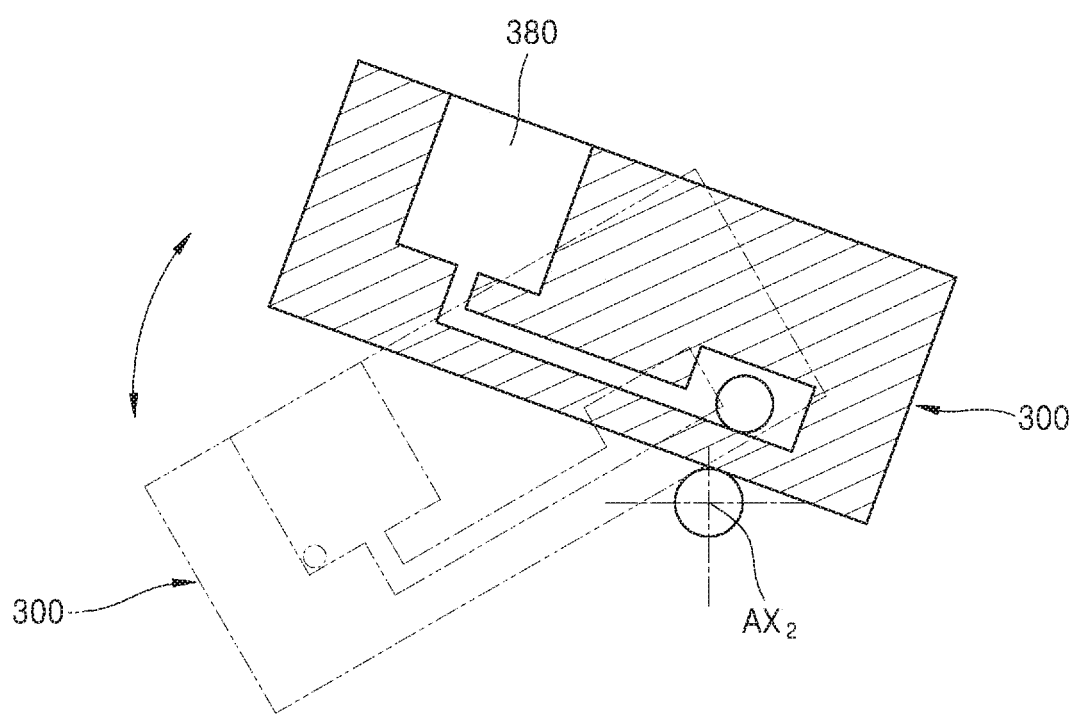
FIG. 12 is a diagram illustrating that the biomimetic chip device of FIG. 8 is tilted about axis $AX_2$.

FIG. 11 is a diagram illustrating that the biomimetic chip device 300 is tilted about axis $AX_1$. FIG. 12 is a diagram illustrating that the biomimetic chip device 300 is tilted about axis $AX_2$.

Referring to FIGS. 8 to 11, axis $AX_1$ may be arranged parallel to the Y axis at the center of the biomimetic chip device 300 in the X-axis direction. As shown in FIG. 8, when the biomimetic chip device 300 is tilted clockwise about axis $AX_1$, the first fluid is provided from the first reservoir 341 to each of the culture chambers 330 through the main channel 320. The first fluid moves to the second reservoir 342 via the culture chambers 330. Conversely, when the biomimetic chip device 300 is tilted counterclockwise about axis $AX_1$, the first fluid moves from the second reservoir 342 to the first reservoir 341.

In addition, when the biomimetic chip device 300 is tilted clockwise about axis $AX_1$, the second fluid stored in the first injection portion 361 is provided to the culture chambers 330 through the first injection tube 351, and then, to the second injection portion 362 through the second injection tube 352. Conversely, when the biomimetic chip device 300 is tilted counterclockwise about axis $AX_1$, the second fluid stored in the second injection portion 362 is supplied to the culture chambers 330 through the second injection tube 352, and then, moves to the first injection portion 361 through the first injection tube 351.

Referring to FIGS. 8 to 10, and FIG. 12, axis $AX_2$ may be arranged at the bottom surface of the biomimetic chip device 300 so as to be parallel to the X-axis. In an embodiment of the present disclosure, axis $AX_2$ may be arranged below the culture model M. As shown in FIG. 12, when the biomimetic chip device 300 is tilted clockwise about axis $AX_2$, the culture model M injected into the loading chamber 380 moves to the culture chambers 330 through the loading channel 370.

As such, the biomimetic chip device 300 according to the present disclosure may simply form a fluid flow by tilting the same based on gravity, without the inclusion of a pump, a microtubule, or a tubing, thereby reducing the size and weight thereof.

Meanwhile, the size of the culture model M may be greater than the size of the internal flow path of the main channel 320. Accordingly, even when the biomimetic chip device 300 is tilted, the culture model M does not move from the corresponding culture chamber to other culture chambers. That is, each culture model M may be cultured in a spatially separated state from other culture models M.

In addition, the biomimetic chip device 300 may further include a multi-electrode array (MEA). The MEA is arranged under the culture model M and measures the electrical signal of the culture model M. For example, the MEA may be arranged under the artificial neural network formed by the culture model M, and chemical stimuli may be applied to the culture model M to measure electrical signals generated from the artificial neural network.

In one or more embodiments, the main channel 320, the culture chambers 330 and the reservoir 340 may each be arranged in a plurality of rows. In one or more embodiments, the biomimetic chip device 300 according to the present disclosure may be configured to correspond to a standard 96 well micro plate format. As a result, the compatibility with existing cell culture automation equipment may be increased, and thus, high-speed mass screening may be put into practical use.

Figure 13:
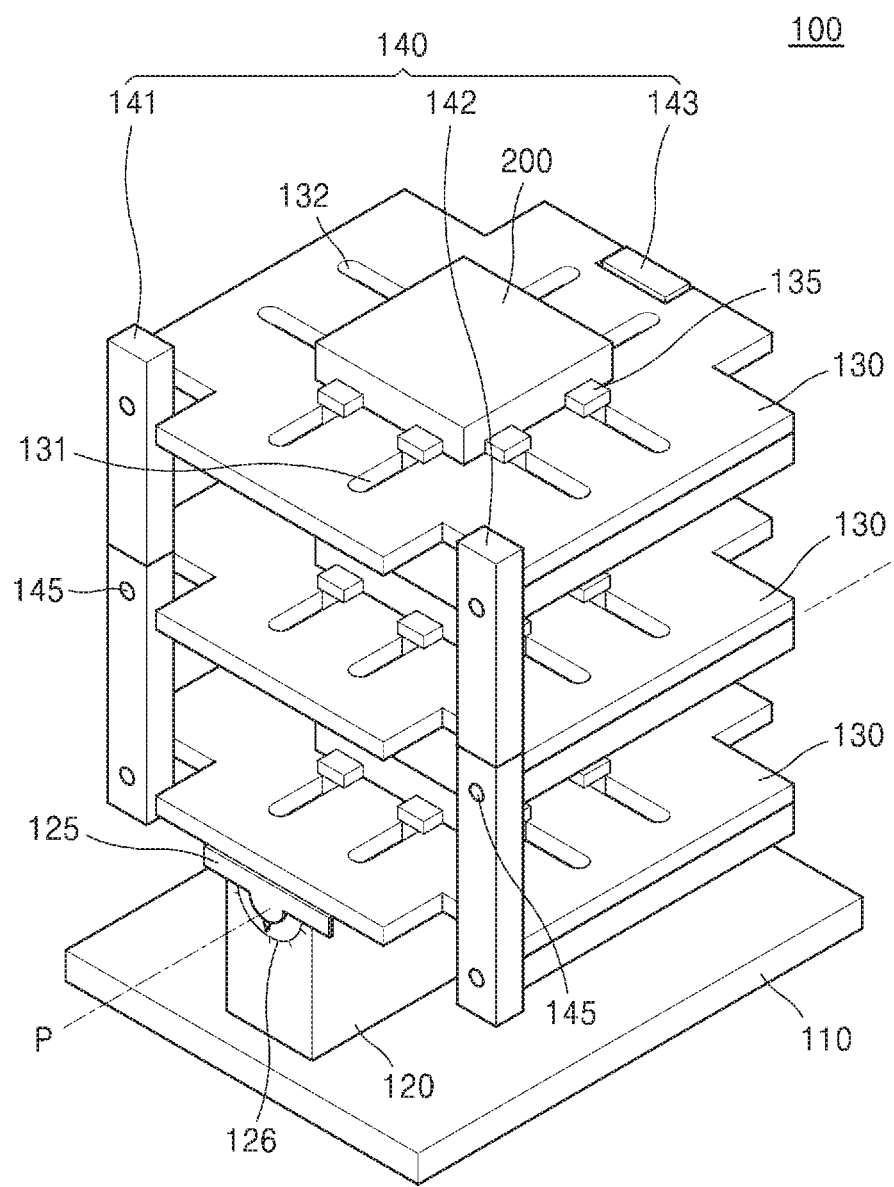
FIG. 13 is a perspective view of a culture apparatus according to another embodiment of the present disclosure.
Figure 14:
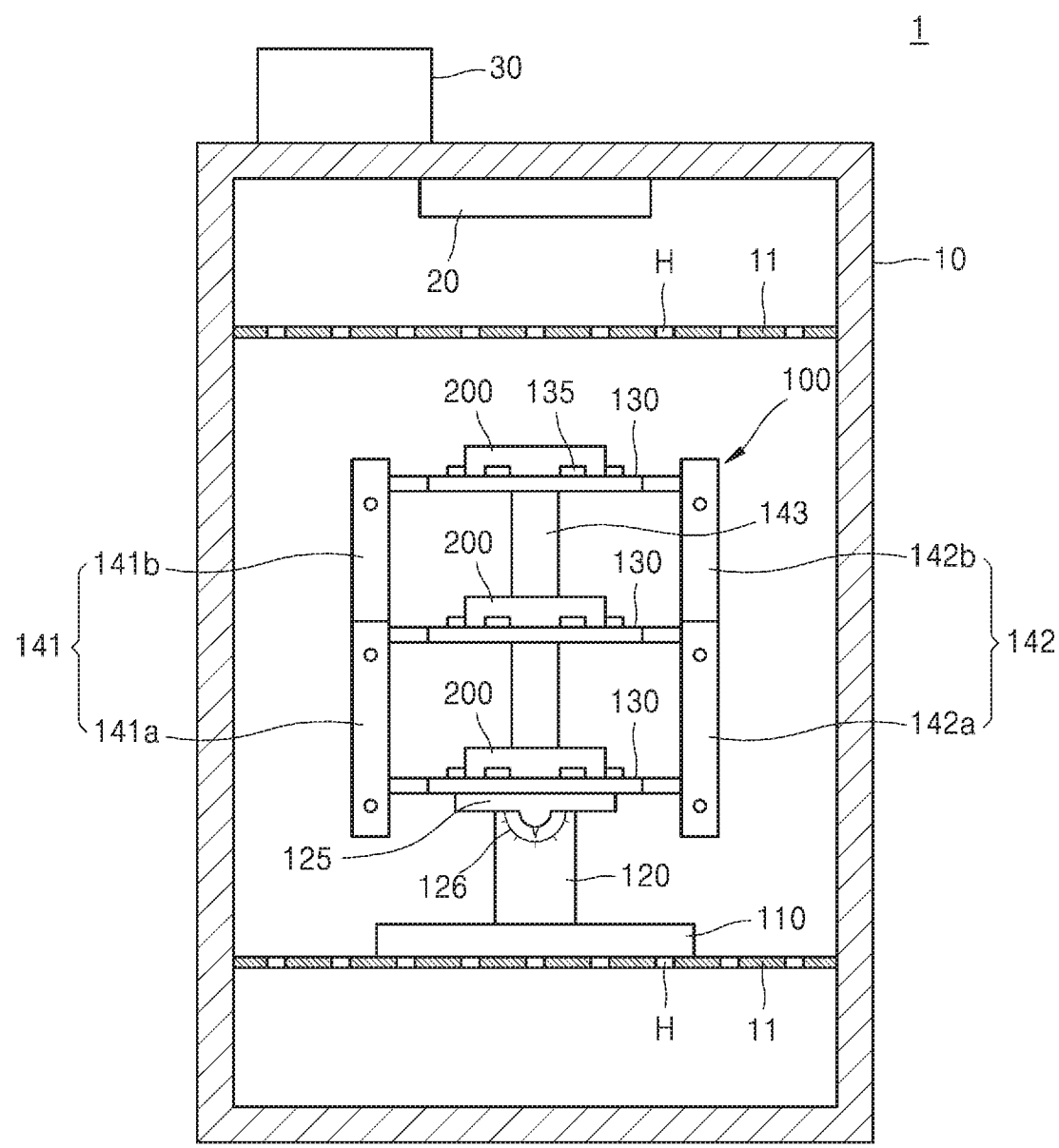
FIG. 14 is a cross-sectional view of a culture chamber system including the culture apparatus of FIG. 13.

FIG. 13 is a perspective view of a culture apparatus 100 according to another embodiment of the present disclosure. FIG. 14 is a cross-sectional view of a culture chamber system 1 including the culture apparatus 100 of FIG. 13.

Referring to FIGS. 13 and 14, the culture apparatus 100 may be provided in the culture chamber system 1 and may culture the cells in the biomimetic chip device 200. Various types of biomimetic chip devices may be provided in the culture apparatus 100, and an embodiment of the present disclosure will be described based on the culture apparatus 100 provided with the biomimetic chip device 200 therein for convenience.

The culture chamber system 1 may include a housing 10, a circulation fan 20, and a controller 30. The culture apparatus 100 of the biomimetic chip device 200 may be provided inside the housing 10. The inner plate 11 is arranged at each of the top and bottom of the housing 10. The inner plate 11 has a plurality of through-holes H so that the air inside the housing 10 may maintain a uniform temperature in the entire area while flowing inside a chamber.

The circulation fan 20 is provided at one side of the housing 10, and may keep the temperature inside the housing 10 constant by flowing air.

The controller 30 may control the culture chamber system 1 and the culture apparatus 100. The controller 30 may control the driving of the circulation fan 20, or control the internal temperature of the culture chamber system 1 by driving a heating unit (not shown) or a cooling unit (not shown). In addition, the controller 30 may drive the driving unit 120 of the culture apparatus 100 to generate a flow of each of the first fluid and the second fluid (hereinafter, referred to as the 'fluid') in the biomimetic chip device 200.

The culture apparatus 100 may include a base 110, the driving unit 120, a support plate 130, and a connection frame 140. The culture apparatus 100 may form a flow of fluid in the inner channel of the biomimetic chip device 200 by tilting the support plate 130 in the left and right directions. That is, the culture apparatus 100 may generate a flow of the fluid based on gravity.

The base 110 has a flat plate shape and is supported at the bottom of the culture chamber system 1. A plurality of the support plates 130 is spaced apart from each other above the base 110.

The driving unit 120 is arranged between the base 110 and the support plates 130. The driving unit 120 may generate a driving force to rotate the support plate 130 and transmit the driving force to the support plate 130. The driving unit 120 is connected to the lower-most support plate of the plurality of the support plates 130. That is, the driving unit 120 may tilt a lower-most support plate alone, or other support plates by the connection frame 140.

The connector 125 may be arranged between the driving unit 120 and the support plates 130. The connector 125 may be provided under the support plates 130, and may be connected to the driving unit 120 to rotate. A tilting display unit 126 is provided on one side of the connector 125 to confirm the tilting angle of the support plate 130.

Figure 15:
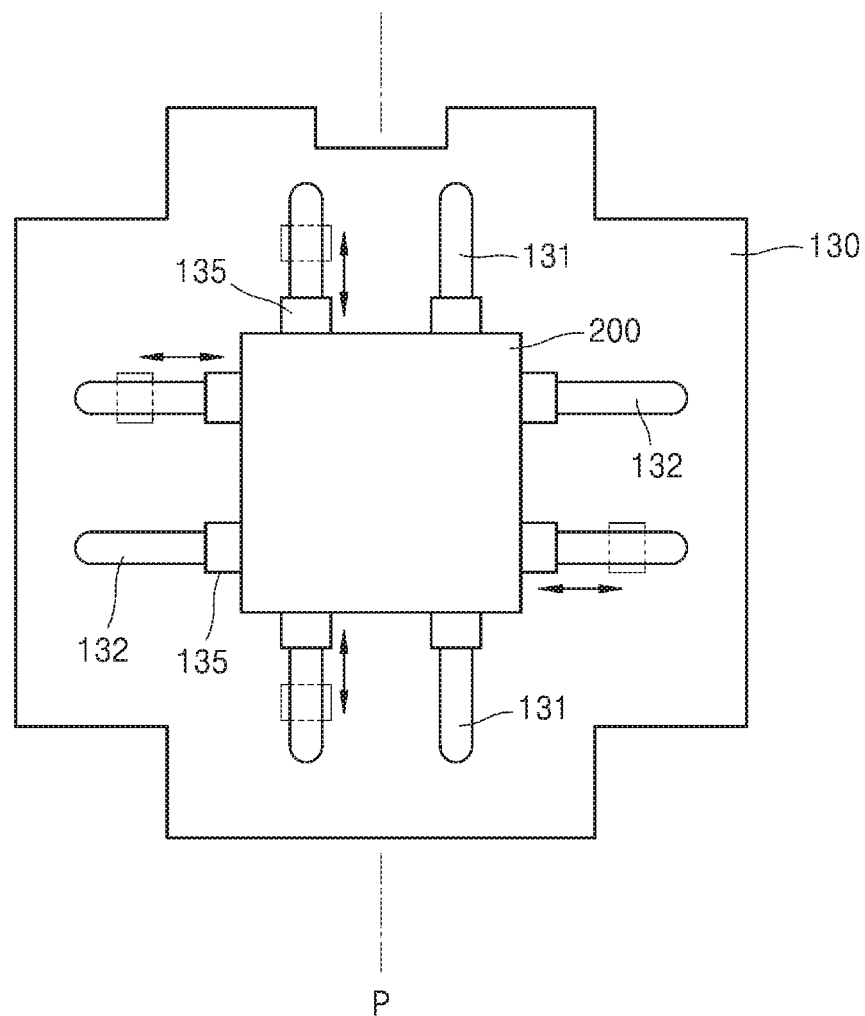
FIG. 15 is a plan view of a support plate of FIG. 13.

FIG. 15 is a plan view illustrating the support plates 130 of FIG. 13.

Referring to FIGS. 13 and 15, there are the plurality of support plates 130, and may be spaced apart from each other in a height direction above the base 110. The biomimetic chip device 200 may be provided on each of the support plates 130.

The support plate 130 is tilted about a first pivot axis P when the driving unit 120 is driven, and the fluid moves to the internal channel of the biomimetic chip device 200 by the inclination of the support plate 130. The first pivot axis P may correspond to axis $AX_1$ of the biomimetic chip device 200 according to the above-described embodiments of the present disclosure.

In one or more embodiments, the support plate 130 may be tilted about a second pivot axis (not shown) perpendicular to the first pivot axis P. That is, when the driving unit 120 is driven, the support plates 130 are tilted about the second pivot axis, and a flow of the fluid is formed inside the biomimetic chip device 200 by the inclination of the support plates 130. In this case, the second pivot axis may correspond to axis $AX_2$ of the biomimetic chip device 200. In this case, a tilting display unit (not shown) for confirming the tilting angle according to axis $AX_2$ may be further provided.

The support plates 130 may have a plurality of guide slits extending in at least two directions. A guide slit extends along the direction in which a clamp 135 moves and may guide the movement of the clamp 135. The guide slit may include a first guide slit 131 extending in the front-rear direction and a second guide slit 132 extending in the width direction.

The clamp 135 is arranged at each of the first guide slit 131 and the second guide slit 132. The clamp 135 may support the sides of the biomimetic chip device 200 in at least two directions. That is, the clamp 135 may move along the first guide slit 131 or the second guide slit 132 while fitting the size of the biomimetic chip device 200, and may fix the position of the biomimetic chip device 200 by holding the sides thereof.

The support plates 130 are equipped with a guide slit and the clamp 135 to accommodate the various sizes of the biomimetic chip device 200.

Figure 16:
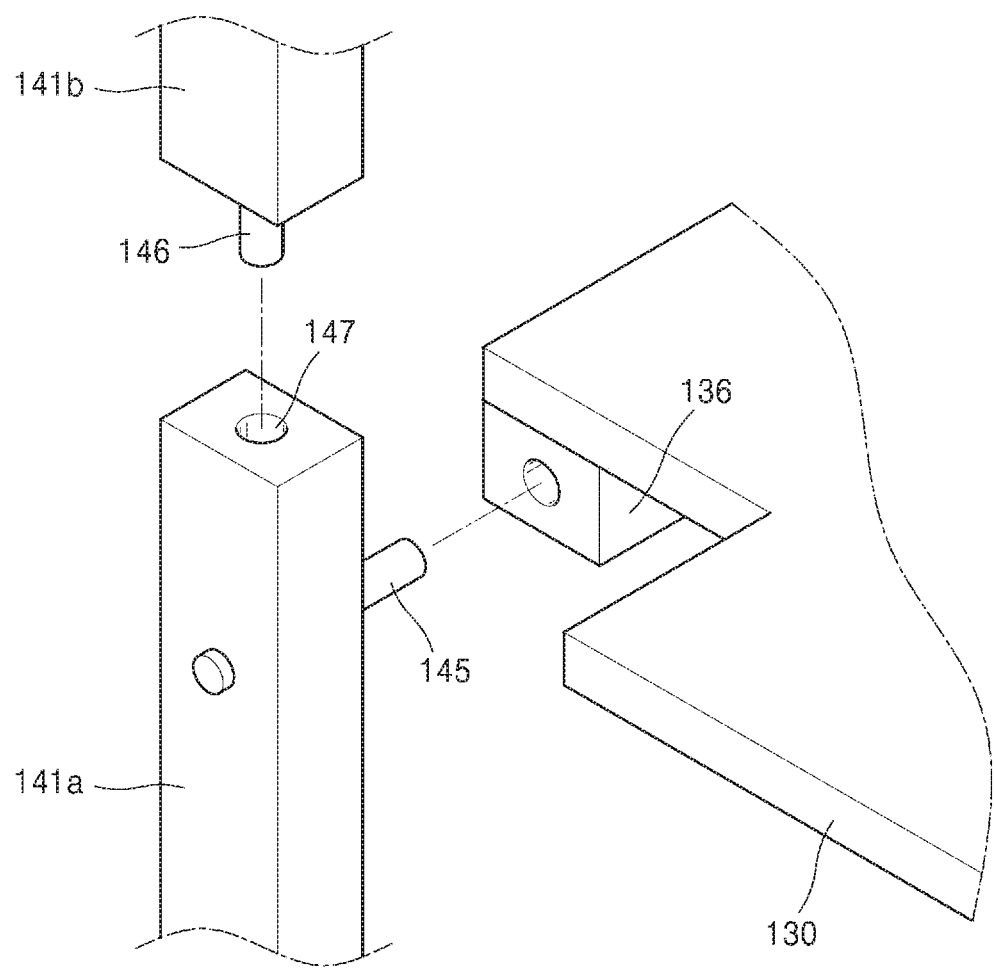
FIG. 16 is a diagram of a coupling relationship between a connection frame and a support plate.

FIG. 16 is a diagram of a coupling relationship between the connection frame 140 and the support plate 130.

Referring to FIGS. 13 and 16, the connection frame 140 may extend in a height direction thereof to connect a plurality of the support plates 130. Also, since the connection frame 140 is rotatably connected to the support plates 130, the support plates 130 may be tilted.

The connection frame 140 is provided to stack the plurality of support plates 130 and includes at least three supporters for balancing. The connection frame 140 may include a first supporter 141 provided on one side of the front side of the support plates 130, a second supporter 142 arranged on the other side of the front side of the support plates 130 to face the first supporter 141, and a third supporter 143 arranged at the center of the rear side of the support plates 130.

The first supporter 141 and the second supporter 142 are arranged on both sides of the front side of the support plates 130. Since no other structure is arranged between the first supporter 141 and the second supporter 142, the biomimetic chip device 200 may be easily provided and removed. In detail, referring to FIG. 13, to provide or remove the biomimetic chip device 200 from a middle support plate from among the support plates 130, the biomimetic chip device 200 may be provided to or removed from the space between the first supporter 141 and the second supporter 142 without disassembling the upper-most support plate from among the support plates 130. In addition, since the other structure is not arranged in the space between the first supporter 141 and the second supporter 142, the biomimetic chip device 200 may be automatically provided or removed by using a transfer device (not shown) outside the culture chamber system 1.

Figure 17A:
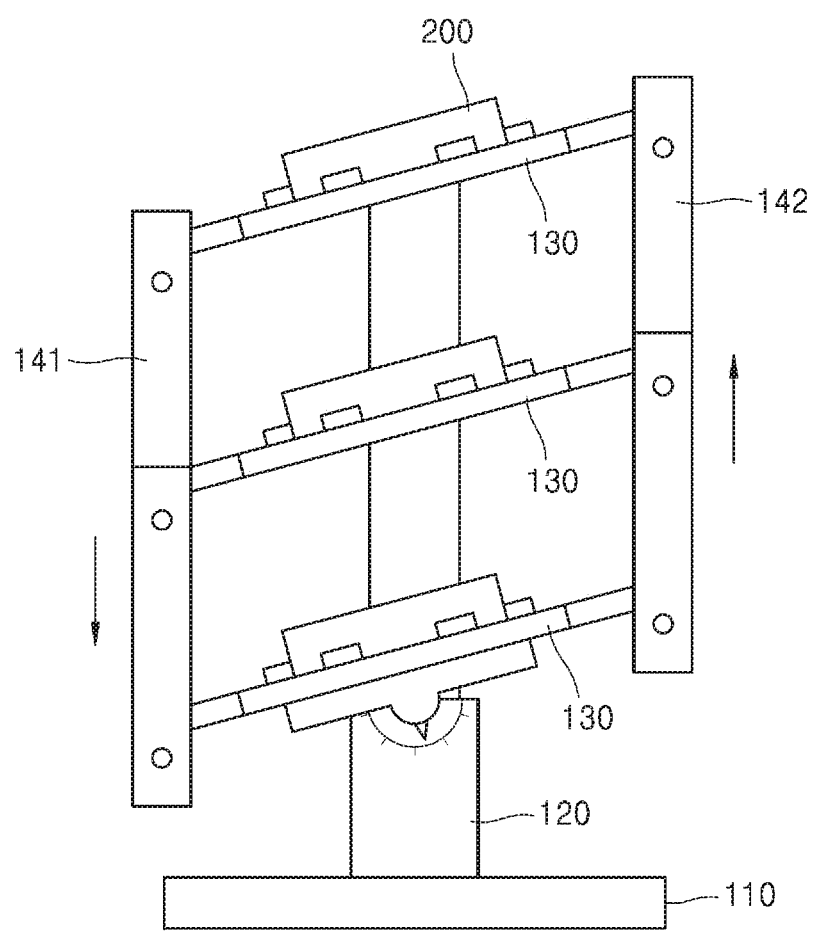
FIG. 17A is a diagram illustrating the driving of a culture apparatus.
Figure 17B:
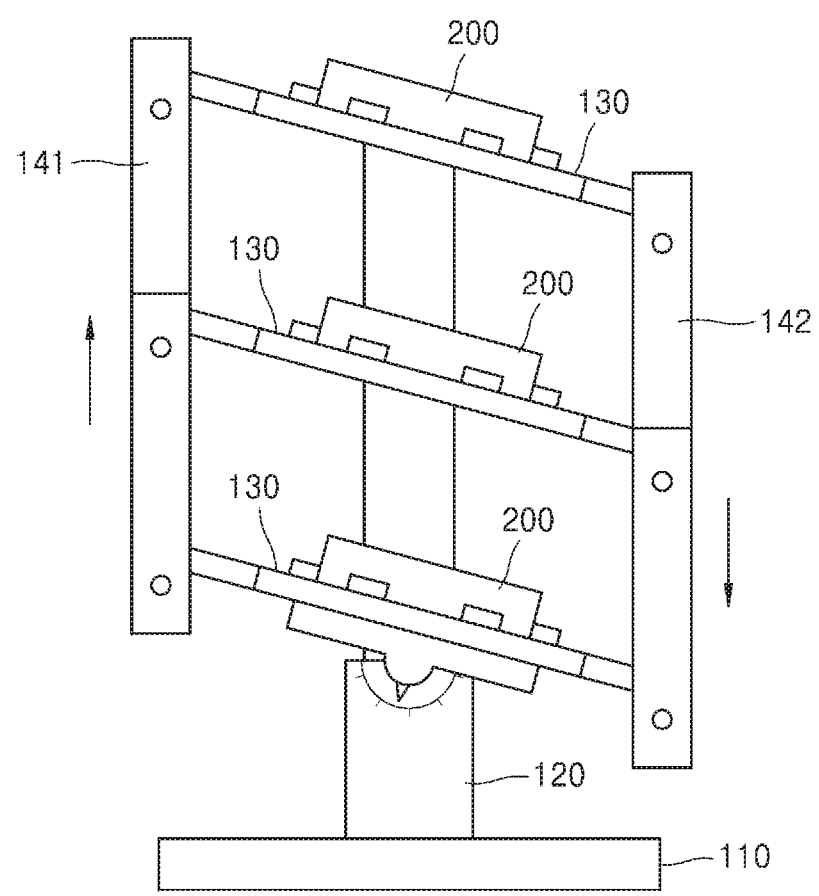
FIG. 17B is a diagram illustrating the driving of a culture apparatus.

As shown in FIGS. 17A and 17B, the first supporter 141 and the second supporter 142 move in opposite directions when the support plates 130 is tilted. That is, when the first supporter 141 ascends, the second supporter 142 descends, and when the first supporter 141 descends, the second supporter 142 ascends. As such, the support plates 130 may be tilted in one direction. However, at this time, the first supporter 141 and the second supporter 142 do not move in the width direction of the support plates 130.

The third supporter 143 may be arranged at the center of the rear side of the support plates 130 to balance the support plates 130. Since the third supporter 143 is arranged at the rear side of the culture chamber system 1, even when the third supporter 143 is arranged at the center of the rear side of the support plate 130, the third supporter 143 may not interfere with the providing or removing of the biomimetic chip device 200.

Since the third supporter 143 is arranged at the center of the rear side of the support plates 130, the balancing may be maintained. Unlike the first supporter 141 and the second supporter 142, the third supporter 143 does not move in the height direction even when the support plates 130 are tilted. Since the position of the third supporter 143 is fixed when the support plate 130 are rotated, the support plate 130 may be stably provided.

The support plates 130 rotate about the first pivot axis P. The first pivot axis P is arranged to penetrate the center of the support plates 130. The first pivot axis P extends from the center between the first supporter 141 and the second supporter 142 towards the third supporter 143.

The connection frame 140 may extend in a height direction by connecting a plurality of connection frames 140. The first supporter 141 may include a first-a supporter 141a and a first-b supporter 141b which are connected to each other, and the second supporter 142 may include a second-a supporter 142a and a second-b supporter 142b which are connected to each other.

Referring to FIG. 16, the first-a supporter 141a and the first-b supporter 141b are connected to each other by inserting a protrusion 146 into an insertion hole 147. That is, the protrusion 146 of the first-b supporter 141b is inserted into the insertion hole 147 of the first-a supporter 141a, thereby allowing the first support 141 to extend in the height direction. In this case, a magnetic material may be arranged on the protrusion 146 or the insertion hole 147 to improve a bonding strength therebetween.

The connection frame 140 is configured in such a way that the support plate 130 rotates. The connection frame 140 includes a pivot pin 145, and the pivot pin 145 is inserted into an opening of a connection end 136 arranged under the support plate 130. Since the pivot pin 145 may rotate at the connection end 136, the support plates 130 can be tilted.

FIG. 17A and FIG. 17B are diagrams illustrating the operation of the culture apparatus 100.

Referring to FIGS. 17A and 17B, in the culture apparatus 100, a flow of fluid may be generated by tilting the support plates 130. When the driving unit 120 rotates in one direction, one side of the support plates 130 and the first supporter 141 descend, and the other side of the support plates 130 and the second supporter 142 ascend. Thus, the fluid moves from the other side of the biomimetic chip device 200 to one side thereof.

In one or more embodiments, when the driving unit 120 rotates in the other direction, one side of the support plates 130 and the first supporter 141 ascend, and the other side of the support plates 130 and the second supporter 142 descend. Thus, the fluid moves from the one side of the biomimetic chip device 200 to the other side thereof.

The tilting angle of the support plates 130 may be controlled by the controller 30. The tilting angle of the support plates 130 determines the flow velocity of the fluid. When the tilting angle of the support plates 130 is large, the velocity of the fluid flowing through the channel of the biomimetic chip device 200 is high, whereas when the tilting angle is small, the velocity of the fluid flowing through the microchannel of the biomimetic chip device 200 is slow. Therefore, the controller 30 adjusts the flow rate of the fluid by controlling the tilting angle of the support plates 130, thereby controlling the culture rate of the culture model.

In addition, the tilting cycle of the support plates 130 may be controlled by the controller 30. Therefore, the controller 30 may change the tilting cycle to adjust the injection timing of the fluid for each culture model.

When the support plates 130 are tilted, the first supporter 141 and the second supporter 142 move in the height direction, but not in the width direction of the support plates 130. The first supporter 141 and the second supporter 142 are pivotally connected to the support plates 130, so when the support plates 130 are tilted, the first supporter 141 and the second supporter 142 move only in the height direction.

When a first supporter and a second supporter move in the width direction, that is, when a connecting frame performs a pendulum motion, the rotation distance of the biomimetic chip device arranged below is different from the rotation distance of the biomimetic chip device arranged above. Therefore, since the flow rate of the fluid in a biomimetic chip device arranged below is different from the flow rate of the fluid in a biomimetic chip device arranged above, the respective layers may not be uniformly cultured.

In addition, when the first supporter and the second supporter move in the width direction, the upper-most support plate swings in the left and right directions, and thus the biomimetic chip device becomes unstable.

However, in the culture apparatus 100 of the biomimetic chip device 200 according to the present disclosure, the first supporter 141 and the second supporter 142 are configured to be rotatable with the support plates 130 so that the first supporter 141 and the second supporter 142 move only in the height direction. As such, the culture apparatus 100 changes only the height of both ends of the biomimetic chip device 200 and does not move the position thereof. As a result, the culture apparatus 100 may form a constant flow of fluid in the biomimetic chip device 200, and may improve stability of the apparatus.

In one or more embodiments, in the culture apparatus 100, the controller 30 adjusts the tilting angle and tilting cycle of the biomimetic chip device 200 to make the fluid to flow in such a way as being suitable for each culture model. For example, a tilting angle of the support plates 130 may be adjusted to control the velocity of the fluid. In addition, the tilting cycle of the support plates 130 may be adjusted to control the injection timing of the fluid.

In addition, the tilting angle of the support plates 130 may be continuously adjusted corresponding to a culture model. For example, when the fluid is to be supplied under different conditions according to the culture model M of the biomimetic chip device 200, the controller 30 may adjust the tilting angle whenever the fluid passes through each of the culture chambers 230.

Through such a configuration, the culture apparatus 100 according to the present disclosure may control the flow rate and the injection timing of the fluid, thereby incubating the culture model M in consideration of the body environment, and performing experiments.

According to the present disclosure, the culture apparatus 100 may flow a fluid by forming a slope in the biomimetic chip device 200 without providing an additional driving source in the biomimetic chip device 200. Since the fluid flows on a gravity-based basis, it is possible to simply move the fluid and supply a quantity of fluid.

According to the present disclosure, the culture apparatus 100 may use various sizes of the biomimetic chip device 200. The clamp 135 of the support plates 130 may be moved along a guide slit, so that various sizes of the biomimetic chip device 200 may be fixed on the support plates 130.

The culture apparatus 100 according to the present disclosure maintains a constant flow quantity of the fluid and ensures structural stability. Since the first supporter 141 and the second supporter 142 are arranged to be rotatable with the support plate 130, the first supporter 141 and the second supporter 142 move only in the height direction and not in the width direction, and thus, the tilting angle and the tilting distance of the support plates 130 are constant at the respective layers. Accordingly, the biomimetic chip device 200 provided in each layer may move a certain amount of fluid and ensure a structural stability thereof.

Figure 18:
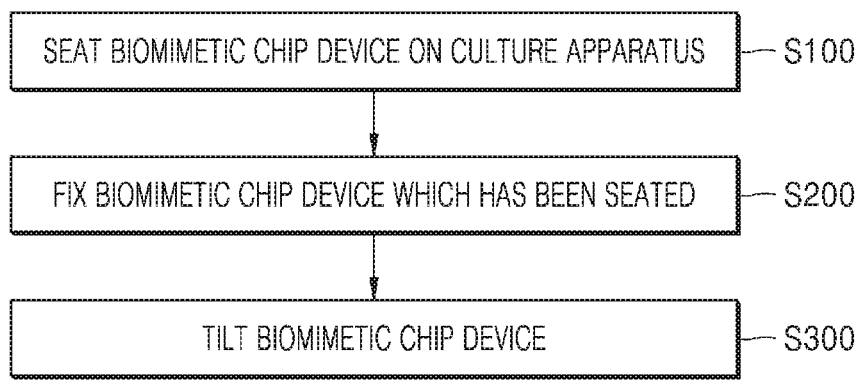
FIG. 18 illustrates a method of culturing a culture model using a culture apparatus according to another embodiment of present disclosure.

FIG. 18 is a view illustrating a culture method using the culture apparatus 100 according to another embodiment of the present disclosure.

Referring to FIG. 18, a culture method using the culture apparatus 100 according to another embodiment of the present disclosure includes seating the biomimetic chip device 200 on the culture apparatus 100 (S100), fixing the biomimetic chip device 200 which has been seated (S200) and tilting the biomimetic chip device 200 (S300).

First, the bottom surface of the body 210 of the biomimetic chip device 200 is seated on the top surface of the support plates 130 of the culture apparatus 100. At this time, the first fluid is injected into the reservoir 240 of the biomimetic chip device 200. In addition, as the culture model M, a non-exposure model $M_A$ is seated in the loading chamber, and an exposure model $M_B$ is seated in the culture unit 250. Corresponding to the number of support plates 130, the plurality of biomimetic chip devices 200 may be seated.

Next, the biomimetic chip device 200, which has been seated, is fixed by the clamp 135. Referring to FIG. 15, with the biomimetic chip device 200 seated on the top surface of the support plates 130, the biomimetic chip device 200 may be supported by moving the clamp 135 along the first guide slit 131 and the second guide slit 132.

Then, the biomimetic chip device 200 may be tilted by operating the driving unit 120 and tilting the support plates 130. As described above, the plurality of the support plates 130 is connected by the connection frame 140. Therefore, even when only the lower-most support plate is tilted according to the operation of the driving unit 120, the remaining support plates may be tilted together.

The tilting of the support plates 130 may include tilting the support plates 130 to seat the culture model M on the culture chamber 230, and tilting the support plates 130 to transfer the first fluid to the culture model M.

Specifically, the driving unit 120 is operated by the controller 30 to tilt the support plates 130 about the second pivot axis (not shown). As described above, the second pivot axis is an axis perpendicular to the first pivot axis P and may correspond to axis $AX_2$. Accordingly, the non-exposure model $M_A$ loaded in the loading chamber moves from the loading chamber along the loading channel to the culture chamber 230. A non-exposure model $M_A$ is mounted in each of the culture chambers 230, and an exposure model $M_B$ is mounted in the culture unit 250. After the non-exposure model $M_A$ is seated in the culture chamber 230, the driving unit 120 may be operated again to tilt the support plates 130 about the second pivot axis, keeping the support plates 130 to be horizontal. The tilting angle may be appropriately adjusted through the controller 30.

Then, the driving unit 120 is operated to tilt the support plate 130 about the first pivot shaft P. In one or more embodiments, by operating the driving unit 120 using the controller 30, when the support plates 130 are rotated clockwise about the first pivot axis P, the first reservoir 241 may be positioned higher than the second reservoir 242. Accordingly, the first fluid stored in the first reservoir 241 is supplied to the culture model M through the main channel 220, and then is supplied to the second reservoir 242. Conversely, when the support plate 130 is rotated counterclockwise about the first pivot axis P, the first fluid stored in the second reservoir 242 is supplied to the culture model M through the main channel 220, and then, supplied to the second reservoir 242. That is, a flow of first fluid may be generated in the biomimetic chip device 200 by tilting the support plate 130.

The tilting angle and the tilting cycle may be appropriately controlled by using the controller 30 to provide the optimal conditions and experimental conditions according to the type and culture timing of the culture model M. In detail, the flow rate of the first fluid may be increased by increasing the tilting angle of the support plates 130, or the flow rate of the first fluid may be decreased by decreasing the tilting angle of the support plates 130. Alternatively, the tilting cycle may be adjusted to control the time when the first fluid is supplied to the culture model M. Also, a tilting angle of the support plates 130 may be continuously adjusted according to the culture model M. For example, when the first fluid must be supplied under different conditions for the non-exposure model $M_A$ and exposure model $M_B$, the tilting angle when the first fluid passes through the non-exposure model $M_A$ and the tilting angle when the first fluid passes through the exposure model $M_B$ may be adjusted to be different from each other by using the controller 30.

In another embodiment, the support plates 130 may be tilted to perform material exchange between the first fluid and the second fluid. For example, the first fluid is supplied to the culture model M by tilting the support plates 130 by rotating the first pivot axis P clockwise, and then, the support plates 130 is tilted by rotating the first pivot axis P counterclockwise. Accordingly, a flow of first fluid is formed in the bypass channel 260, and a flow of the second fluid is formed in the sub-channel 280. The material exchange between the first fluid and the second fluid occurs through the membrane 290 at the boundary interface between the bypass channel 260 and the sub-channel 280. That is, waste and the like may move from the first fluid to the second fluid, and nutrients and the like may move from the second fluid to the first fluid.

In one or more embodiments, when the culture model M is cultured using a culture apparatus 100 equipped with the biomimetic chip device 300 according to presented disclosure, the support plates 130 may be tilted so as to supply the second fluid stored in the injection chamber 360 to the culture chambers 330. For example, as the culture model M in the biomimetic chip device 300 is incubated, the neural protrusions extending from the culture model M may narrow the flow cross-section of the main channel 320. Accordingly, the fluid flow resistance in the main channel 320 is increased, so that the first fluid may not flow smoothly. In this case, when the second fluid is injected into the injection chamber 360 of the biomimetic chip device 300 and then the support plates 130 are tilted about the first pivot axis P, the second fluid is provided from the injection chamber 360 to the culture model M. In this case, the second fluid may be the same as the first fluid.

In one or more embodiments, in the case of using the biomimetic chip device 300 according to present disclosure, the support plates 130 may be tilted so as to impart different chemical stimuli to each of the culture models M. For example, the second fluid is injected into the injection chamber 360 of the biomimetic chip device 300. In this case, different types of the second fluid may be injected into the injection chamber 360, and the second fluid may be a drug for imparting a chemical stimulus to the culture model M. Next, when the support plates 130 are tilted about the first pivot axis P, the second fluid is supplied from the injection chamber 360 to the culture model M. As such, the culture models M imparted with the chemical stimuli by the second fluids may display different electrical signals.

In one or more embodiments, the method may further include measuring an electrical signal of the culture model M of the biomimetic chip device 300 according to the present disclosure. For example, in the culture apparatus 100 equipped with the biomimetic chip device 300 having the MEA, as described above, the support plates 130 may be tilted about the first pivot axis P to impart a chemical stimulus to the culture model M. Accordingly, electrical signals generated from the culture model M may be measured. In this case, the culture apparatus 100 may further include a display member connected to the MEA to visually display the electrical signal generated by the culture model M.

In the case of a conventional cell culture apparatus, two-dimensional cell models are cultured in a static environment to form up to two neural networks. However, such a conventional cell culture device is focused on the convenience of the experiment, and is poor in terms of the actual biocompatibility. For example, in the case of the two-dimensional cell model, the cell model has a flat shape and is stretched on a surface, all cells are uniformly exposed to the culture solution and the drug, and the connections between the cells are made only in one direction. As such, the two-dimensional cell model is different from the actual living body. In addition, since the cell model is statically cultured, it is impossible to implement cell culture conditions that reflect the actual living environment.

However, the culture model M according to an embodiment of the present disclosure is a three-dimensional organoid model, the shape of the cell model has a morphology (such as an ellipsoid) in the actual living body, there is a concentration gradient of culture medium and drug in the cell model, like in the actual biological environment, and intercellular connectivity is made in all aspects of the cell, thereby providing an environment similar to the actual biological environment. In addition, the biomimetic chip device according to an embodiment of the present disclosure can implement a cell culture condition reflecting the actual living environment by culturing a three-dimensional organoid model in a dynamic culturing environment.

A biomimetic chip device according to the present disclosure may simply form a fluid flow by tilting the same based on gravity, without the inclusion of a pump or a microtubule, thereby reducing the size and weight thereof.

In addition, the biomimetic chip device according to the present disclosure may embody the same culturing environment as the actual biological environment by including a culture model for the unexposed and exposed organs in the living body, and controlling the flow of the fluid in the same manner as applied to the flow of blood in the living body.

In addition, the biomimetic chip device according to present disclosure may be arranged in culture chambers such that culture models are spatially separated from each other, and different drugs are supplied to the culture models to selectively stimulate a specific culture model.

In addition, the biomimetic chip device according to the present disclosure may implement the actual living body network by connecting the culture models to be cultured in the culture chambers. In particular, by culturing different neural cell models that simulate specific parts of the living body as a culture model to form artificial neural networks, it is possible to effectively observe the response in the artificial neural network when a specific culture model is stimulated.

A biomimetic chip device according to the present disclosure may simply form a fluid flow by tilting the same based on gravity, without the inclusion of a pump or a microtubule, thereby reducing the size and weight thereof.

In addition, the biomimetic chip device according to the present disclosure may embody the same culturing environment as the actual biological environment by including a culture model for the unexposed and exposed organs in the living body, controlling the flow of the fluid in the same manner as applied to the flow of blood in the living body, and moving a target material through a membrane formed in a bypass channel to simulate the discharge of material in vivo.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without leaving from the spirit and scope of the disclosure as defined by the following claims.

What is claimed is:

1. A biomimetic chip device comprising:
    a body;
    a main channel located in the body, wherein the main channel extends in one direction;
    a plurality of culture chambers spaced apart from each other, wherein the plurality of culture chambers are located on the main channel so as to overlap with a flow path of the main channel;
    a first reservoir positioned at a first end of the main channel, wherein the first reservoir is configured to store a first fluid; and
    a second reservoir arranged at a second end of the main channel, wherein the second reservoir is configured to store the first fluid,
    wherein the body is rotatable to tilt about a first axis perpendicular to the one direction to allow the first fluid to flow between the first reservoir and the second reservoir.

2. The biomimetic chip device of claim 1, wherein
    in the biomimetic chip device, the plurality of culture chambers are configured to house respective culture models, wherein the culture models are arranged in the one direction according to an order in which blood is supplied in a living body.

3. The biomimetic chip device of claim 2, wherein
    the culture models comprise a non-exposure model of the inside of the living body and an exposure model of the outside of the living body, and
    the first fluid is configured to flow from the first reservoir to the second reservoir through the culture chambers culturing the non-exposure model and the exposure model.

4. The biomimetic chip device of claim 1, further comprising
    a bypass channel positioned in parallel with the main channel, wherein the bypass channel is configured to return, to the first reservoir, the first fluid which has moved from the first reservoir to the second reservoir.

5. The biomimetic chip device of claim 4, wherein
    when the body is tilted in a first direction, the first fluid moves along the main channel; and
    when the body is tilted in a second direction opposite to the first direction, the first fluid moves along the bypass channel.

6. The biomimetic chip device of claim 4, further comprising:
    a first valve unit arranged at both the first end of the main channel and the second end of the main channel; and
    a second valve unit arranged at both a first end of the bypass channel and a second end of the bypass channel.

7. The biomimetic chip device of claim 6, wherein
    each of the first valve unit and the second valve unit is a ball valve for moving the first fluid in a pre-set flow direction.

8. The biomimetic chip device of claim 4, further comprising:
    a sub-channel configured to channel a second fluid, wherein a portion of the sub-channel is positioned in parallel with the bypass channel; and
    wherein the first fluid moving through the bypass channel exchanges material with the second fluid moving through the sub-channel.

9. The biomimetic chip device of claim 8, further comprising:
    a membrane between the bypass channel and the sub-channel.

10. The biomimetic chip device of claim 8, wherein
    in the bypass channel and the sub-channel, the first fluid and the second fluid exchange materials when the body rotates in a pre-set direction.

* * * * *